(12) United States Patent
Gu et al.

(10) Patent No.: US 9,856,315 B2
(45) Date of Patent: Jan. 2, 2018

(54) METHYLATION AND ACETYLATION SITES

(71) Applicant: Cell Signaling Technology, Inc., Danvers, MA (US)

(72) Inventors: Hongbo Gu, Princeton, NJ (US); Ailan Guo, Lexington, MA (US); Daniel Mulhern, Beverly, MA (US); Jeffrey C. Silva, Beverly, MA (US); Jing Zhou, Beverly, MA (US)

(73) Assignee: Cell Signaling Technology, Inc., Danvers, MA (US)

( * ) Notice: Subject to any disclaimer, the term of this patent is extended or adjusted under 35 U.S.C. 154(b) by 0 days.

(21) Appl. No.: 14/884,327

(22) Filed: Oct. 15, 2015

(65) Prior Publication Data
US 2016/0137725 A1    May 19, 2016

Related U.S. Application Data

(60) Provisional application No. 62/064,253, filed on Oct. 15, 2014.

(51) Int. Cl.
*G01N 33/53* (2006.01)
*C07K 16/18* (2006.01)
*G01N 33/543* (2006.01)

(52) U.S. Cl.
CPC .......... *C07K 16/18* (2013.01); *G01N 33/543* (2013.01); *C07K 2317/22* (2013.01); *C07K 2317/24* (2013.01); *C07K 2317/31* (2013.01); *C07K 2317/54* (2013.01); *C07K 2317/55* (2013.01); *C07K 2317/622* (2013.01); *C07K 2317/626* (2013.01); *C07K 2317/76* (2013.01); *G01N 2440/00* (2013.01)

(58) Field of Classification Search
None
See application file for complete search history.

(56) References Cited

PUBLICATIONS

Guo A. et al., "Immunoaffinity Enrichment and Mass Spectrometry Analysis of Protein Methylation", Molecular & Cellular Proteomics 13:372-387 (2014).

*Primary Examiner* — Jacob Cheu
(74) *Attorney, Agent, or Firm* — Scully, Scott, Murphy & Presser, P.C.

(57) ABSTRACT

The disclosure features over 5000 methylation and acetylation sites identified in human cell line, human serum and mouse tissues, peptides (including AQUA peptides) comprising a methylation or acetylation site of the disclosure, antibodies specifically bind to a methylation or acetylation site of the disclosure, and diagnostic and therapeutic uses of the above.

10 Claims, No Drawings

METHYLATION AND ACETYLATION SITES

FIELD OF THE DISCLOSURE

The disclosure relates generally to arginine and lysine methylation and acetylation sites, methods and compositions for detecting, quantitating and modulating the same.

REFERENCE TO TABLE

This application contains references to two tables ("Table 1" and "Table 2") which are being submitted concurrently herewith as the text file "CST335Table1.txt" and CST335Table2.txt, file size 471 kB and 50 kB respectively, created on Oct. 14, 2015. The aforementioned tables are incorporated herein by reference in their entirety.

BACKGROUND

Protein methylation and acetylation are common post-translational modification that mostly occurs on arginine or lysine residues. Arginine methylation has been reported to regulate RNA processing, gene transcription, DNA damage repair, protein translocation, and signal transduction. Lysine methylation is best known to regulate histone function and is involved in epigenetic regulation of gene transcription.

Protein methyltransferases and demethylases have been implicated in human health and disease (Greer, E. L., and Shi, Y. (2012) *Histone methylation: a dynamic mark in health, disease and inheritance. Nature Reviews. Genetics* 13, 343-357; Yang, Y, and Bedford, M. T. (2013) *Protein arginine methyltransferases and cancer. Nature Reviews. Cancer* 13, 37-50). Considering the important biological roles of protein methylation, there is a need for identification of additional methylated proteins and methylation sites.

SUMMARY

The disclosure features in one aspect arginine and lysine methylation sites found in human cell lines, human serum and mouse tissues (Table 1) and lysine acetylation sites found in human serum (Table 2). The sites occur in proteins such as: secreted proteins, adaptor/scaffold proteins, non-receptor ser/thr protein kinases, non-receptor tyrosine protein kinases, chromatin/DNA binding/repair/replication proteins, cytoskeletal proteins, mitochondrial proteins, transcriptional regulators, translational regulators, ubiquitin conjugating system, cell cycle regulation proteins, RNA processing proteins, adhesion or extracellular matrix proteins, proteases, kinases, apoptosis proteins, chaperone proteins, receptor/channel/transporter/cell surface proteins, enzymes, G proteins or regulator proteins, Endoplasmic reticulum or golgi proteins, calcium-binding proteins, vesicle proteins, motor or contractile proteins, non-protein kinases, phosphatases, and proteins of unknown function.

In another aspect, the disclosure features peptides comprising the methylation or acetylation sites of the disclosure, and proteins and peptides that are mutated to eliminate the methylation or acetylation.

In another aspect, the disclosure features modulators that modulate arginine and lysine methylation or acetylation at a methylation or acetylation site of the disclosure, including small molecules, peptides comprising a methlyation site or acetylation site, and binding molecules that specifically bind at a methylation or acetylation site or acetylation site, including but not limited to antibodies or antigen-binding fragments thereof.

In another aspect, the disclosure features compositions for detecting, quantitating or modulating a methylation or acetylation site of the disclosure, including peptides comprising a methylation or acetylation site and antibodies that specifically bind at a methylation or acetylation site. As used herein, an "antibody" or "antibodies" is meant to also encompass antibody binding fragments, including but not limited to, partial or full heavy chains or light chains, variable regions, or CDR regions of any methylation or acetylation site-specific antibodies described herein. In another embodiment, the antibody is a polyclonal antibody, a monoclonal antibody or antibody fragment, a recombinant antibody, a camelid antibody, a bispecific antibody, a diabody, a chimerized or chimeric antibody or antibody fragment, a humanized antibody or antibody fragment, a deimmunized human antibody or antibody fragment, a fully human antibody or antibody fragment, a single chain antibody, an Fv, an Fd, an Fab, an Fab', and an F(ab')$_2$. In certain embodiments, the compositions for detecting, quantitating or modulating a methylation or acetylation site of the disclosure are Heavy-Isotype Labeled Peptides (AQUA peptides) comprising a methylation or acetylation site.

In another aspect, the disclosure features methylation or acetylation site specific antibodies. In one embodiment, the antibodies specifically bind to an amino acid sequence comprising a methylation identified in Table 1 or acetylation site identified in Table 2 when the arginine or lysine identified in Column E is methylated, and do not significantly bind when the arginine or lysine is not methylated. In another embodiment, the antibodies specifically bind to an amino acid sequence comprising a methylation or acetylation site when the arginine or lysine is not methylated, and do not significantly bind when the lysine is methylated. In another embodiment, the antibodies are monoclonal or polyclonal antibodies.

In another aspect, the antibody inhibits tumor growth, inhibits cancer cell proliferation, inhibits cancer cell migration, inhibits metastasis of cancer cells, inhibits angiogenesis, or induces apoptosis. In one embodiment, the antibody is conjugated to a cytotoxic agent. In another embodiment, the cytotoxic agent is selected from the group consisting of a radiotherapeutic agent, a ribosome-inactivating protein (RIP), a chemotherapeutic agent, a cytotoxic small molecule, a cytotoxic peptide, and a cytotoxic protein.

In another aspect, the disclosure features a method for making methylation or acetylation site-specific antibodies.

In another aspect, the disclosure features compositions comprising a peptide, protein, or antibody of the disclosure, including pharmaceutical compositions.

In a further aspect, the disclosure features methods of treating or preventing cancer in a subject, wherein the cancer is associated with the methylation state of a methylation site in Table 1 or acetylation site in Table 2, whether methylated or not methylated. In certain embodiments, the methods comprise administering to a subject a therapeutically effective amount of a peptide comprising a methylation or acetylation site of the disclosure. In certain embodiments, the methods comprise administering to a subject a therapeutically effective amount of an antibody or antigen-binding fragment thereof that specifically binds at a methylation or acetylation site of the disclosure, whether methylated or not methylated, or acetylated or not acetylated, respectively. In another embodiment, the peptide or antibody reduces the at least one biological activity of a targeted signaling protein. In another embodiment, the biological activity of a targeted signaling is ligand binding or down-stream signal transduction. In another embodiment the antibody is conjugated to a cytotoxic agent (e.g., a radiotherapeutic agent, a ribosome-inactivating protein (RIP), a chemotherapeutic agent, a toxic small molecule, a toxic peptide, and a toxic protein).

In another aspect, the disclosure features methods of diagnosing carcinoma in a subject, wherein the carcinoma is associated with arginine or lysine methylation or acetylation or demethylation or deacetylation at a methylation site in Table 1 or acetylation site in Table 2. In one embodiment, the methylation or acetylation state or level at the arginine or lysine position identified in the corresponding row in Column E of Table 1 or Table 2 is determined to be present or not present in a biological sample. In another embodiment the methylation or acetylation state or level at the methylation or acetylation site, as compared to a control, is determined. In another embodiment the methylation or acetylation state or level is determined by an antibody that specifically binds to the methylation or acetylation site, when methylated or when not methylated. In a further embodiment an AQUA peptide, methylated at the arginine or lysine site, is used to identify and/or quantify.

In a further aspect, the disclosure features methods for detecting and quantitating methylation or acetylation at an arginine or lysine methylation or acetylation site of the disclosure.

In another aspect, the disclosure features a method for identifying an agent that modulates arginine or lysine methylation or acetylation at a methylation or acetylation site of the disclosure, comprising: contacting a peptide or protein comprising a methylation or acetylation site of the disclosure with a candidate agent, and determining the methylation or acetylation state or level at the methylation or acetylation site. A change in the methylation or acetylation state or level at the specified arginine or lysine in the presence of the test agent, as compared to a control, indicates that the candidate agent potentially modulates arginine or lysine methylation or actylation at a methylation or acetylation site disclosed.

In another aspect, immunoassays for binding, purifying, quantifying and otherwise generally detecting the methylation or acetylation of a protein or peptide at a methylation or acetylation site are disclosed.

Another embodiment provides a method comprising: (a) obtaining a digested proteinaceous preparation comprising a digested biological sample; (b) contacting the proteinaceous preparation with an immobilized antibody or antibody fragment that binds to a recurring protein motif or to a post-translational modification in a context-independent manner; and (c) isolating a population of peptides specifically bound by the immobilized antibody or antibody fragment; wherein the biological sample is not immunodepleted of one or more proteins selected from the group consisting of: alpha 1-acid glycoprotein, alpha 1-antitrypsin, alpha 2-macroglobulin, albumin, apolipoprotein A1, apolipoprotein A2, apolipoprotein B, fibrinogen, haptoglobin, IgA, IgD, IgG, IgM, transferrin, complement C3, complement C4, complement C1q, ceruloplasmin, prealbumin, and plasminogen. In on aspect, the biological sample is not immunodepleted of any combination of one or more proteins selected from the group consisting of: alpha 1-acid glycoprotein, alpha 1-antitrypsin, alpha 2-macroglobulin, albumin, apolipoprotein A1, apolipoprotein A2, apolipoprotein B, fibrinogen, haptoglobin, IgA, IgD, IgG, IgM, transferrin, complement C3, complement C4, complement C1q, ceruloplasmin, prealbumin, and plasminogen.

In one aspect said biological sample is digested utilizing a reagent selected from the group consisting of cyanogen bromide, BNPS-Skatole, formic acid, trypsin, Lysine-C endopeptidase (LysC); arginine-C endopeptidase (ArgC), Asp-N, glutamic acid, endopeptidase (GluC), chymotrypsin, and combinations thereof. In one aspect the reagent is trypsin. In another aspect, the biological sample is derived from saliva, mucous, tears, blood, serum, lymph fluids, buccal cells, circulating tumor cells, mucosal cells, biopsy tissue, cerebrospinal fluid, semen, feces, plasma, urine, a suspension of cells, or a suspension of cells and viruses. Another aspect provides that the biological sample is derived from serum or plasma.

In another aspect, the antibody or antibody fragment is selected from the group consisting of a polyclonal antibody, a monoclonal antibody or antibody fragment, a recombinant antibody, a camelid antibody, a bispecific antibody, a diabody, a chimerized or chimeric antibody or antibody fragment, a humanized antibody or antibody fragment, a deimmunized human antibody or antibody fragment, a fully human antibody or antibody fragment, a single chain antibody, an Fv, an Fd, an Fab, an Fab', and an $F(ab')_2$. In another aspect the antibody is a polyclonal antibody. In another aspect, the antibody is a monoclonal antibody.

Also featured are pharmaceutical compositions and kits comprising one or more antibodies or peptides of the disclosure and methods of using them.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Reference is made herein to various methodologies and materials known to those of skill in the art. Standard reference works setting forth the general principles of recombinant DNA technology include Sambrook et al., Molecular Cloning: A Laboratory Manual, 2nd Ed., Cold Spring Harbor Laboratory Press, New York (1989); Kaufman et al., Eds., Handbook of Molecular and Cellular Methods in Biology in Medicine, CRC Press, Boca Raton (1995); McPherson, Ed., Directed Mutagenesis: A Practical Approach, IRL Press, Oxford (1991). Standard reference works setting forth the general principles of antibody technology include Greenfield, Ed., Antibodies: A Laboratory Manual, 2d Ed., Cold Spring Harbor Laboratory Press, New York (2014); Coligan et al., Eds., Current Protocols in Immunology, DOI: 10.1002/0471142735 (February 2014); and Lo, Ed., Antibody Engineering: Methods and Protocols, Humana Press, Totawa, N.J. (2004). Standard reference works setting forth the general principles of pharmacology include Goodman and Gilman's The Pharmacological Basis of Therapeutics, 11th Ed., McGraw Hill Companies Inc., New York (2006). The above reference works are incorporated by reference herein in their entireties.

As used herein, the following terms have the meanings indicated. As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth.

In general, the term "about" is used herein to modify a numerical value above and below the stated value by a variance of 20%. Where combinations of alternatives are provided (e.g., combinations of alternative CDR sequences or combinations of alternative light and/or heavy chain sequences), the description includes each combination taken individually, as well as combinations of subsets of the alternatives.

Other features and advantages of the invention will be apparent from the following detailed description, and from the claims.

DETAILED DESCRIPTION

Disclosed are arginine and lysine methylation or acetylation sites in signaling proteins extracted from mouse brain, mouse embryo, human serum, and HTC116 cell line. The newly discovered methylation and acetylation sites significantly extend our knowledge of methyltranferase substrates and of the proteins in which the sites occur. The disclosure of the methylation or acetylation sites and reagents including peptides and antibodies specific for the sites add important new tools for the elucidation of signaling pathways that are associate with a host of biological processes including cell division, growth, differentiation, develomental changes and disease. Their discovery provides and focuses further elucidation of the role and function of protein methylation and acetylation in cell biology. Additionally, the sites provide additional diagnostic and therapeutic targets.

Methylation and Acetylation Sites

In one aspect, the disclosure features arginine and lysine methylation or acetylation sites in signaling proteins from cellular extracts from mouse brain and mouse embryo samples, human serum, and from the human HCT 116 cell line (see further description below in Examples), identified using the techniques described in Rush et al., "Immunoaffinity Isolation of Modified Peptides From Complex Mixtures," U.S. Pat. Nos. 7,198,896 and 7,300,753. Table 1 summarizes the identified methylation and Table 2 summerizes the identified acetylation sites.

These methylation or acetylation sites thus occur in proteins found in various diseases. The sequences of the human homologues are publicly available in SwissProt database and their Accession numbers listed in Column C of Table 1 and Table 2. The sites occur in proteins such as: secreted proteins, adaptor/scaffold proteins, non-receptor ser/thr protein kinases, non-receptor tyrosine protein kinases, chromatin/DNA binding/repair/replication proteins, cytoskeletal proteins, mitochondrial proteins, transcriptional regulators, translational regulators, ubiquitin conjugating system, cell cycle regulation proteins, RNA processing proteins, adhesion or extracellular matrix proteins, proteases, kinases, apoptosis proteins, chaperone proteins, receptor/channel/transporter/cell surface proteins, enzymes, G proteins or regulator proteins, Endoplasmic reticulum or golgi proteins, calcium-binding proteins, vesicle proteins, motor or contractile proteins, non-protein kinases, phosphatases, and proteins of unknown function (see Column E of Table 1 or Table 2).

The methylation or acetylation sites of the disclosure were identified according to the methods described by Rush et al., "Immunoaffinity Isolation of Modified Peptides From Complex Mixtures," U.S. Pat. Nos. 7,198,896 and 7,300,753, and which are herein incorporated by reference in its entirety. The sites of the disclosure were discovered using a modification of the method described in Gygi et al., U.S. Patent Publication No. 20060148093 (herein incorporated by reference in its entirety) which describes a method for detecting and quantifying proteins (and post-translational protein modifications such as methylation) by mass spectrophotometry analysis using peptide internal standards.

Briefly, the methylation or acetylation sites of the disclosure were isolated and characterized by immunoaffinity isolation and mass-spectrometric characterization (IAP), using various cell lines and tissues from mice and humans (see Column F of Table 1 or Table 2). In addition to the newly discovered methylation or acetylation sites (all having a methylatable arginine or lysine or an acetylatable lysine), many known methylation or acetylation sites were also identified. The immunoaffinity/mass spectrometric technique described in Rush et al, i.e., the "IAP" method, is described in detail in the Examples and briefly summarized below.

The IAP method generally comprises the following steps: (a) a proteinaceous preparation (e.g., a digested cell extract) comprising methylated peptides from two or more different proteins is obtained from an organism; (b) the preparation is contacted with at least one immobilized general methylated residue (e.g., methyl-lysine or methyl-arginine)-specific antibody; (c) at least one methylated peptide specifically bound by the immobilized antibody in step (b) is isolated; and (d) the modified peptide isolated in step (c) is characterized by mass spectrometry (MS) and/or tandem mass spectrometry (MS-MS). Subsequently, (e) a search program (e.g., Sequest) may be utilized to substantially match the spectra obtained for the isolated, modified peptide during the characterization of step (d) with the spectra for a known peptide sequence. A quantification step, e.g., using SILAC or AQUA, may also be used to quantify isolated peptides in order to compare peptide levels in a sample to a reference or baseline.

In the IAP method as disclosed herein, a general methylated lysine-specific or arginine-specific monoclonal antibody may be used in the immunoaffinity step to isolate the widest possible number of methylated-lysine or methylated-arginine containing peptides from the cell extracts.

As described in more detail in the Examples, lysates may be prepared from various cell lines or tissue samples and digested with a protease (e.g., trypsin) after treatment with DTT and iodoacetamide to alkylate cysteine residues. Before the immunoaffinity step, peptides may be pre-fractionated (e.g., by reversed-phase solid phase extraction using Sep-Pak $C_{18}$ columns) to separate peptides from other cellular components. The solid phase extraction cartridges may then be eluted (e.g., with acetonitrile). Each lyophilized peptide fraction can be redissolved and treated with a methyl-lysine or methyl-arginine specific antibody immobilized on protein Agarose. Immunoaffinity-purified peptides can be eluted and a portion of this fraction may be concentrated (e.g., with Stage or Zip tips) and analyzed by LC-MS/MS (e.g., using a ThermoFinnigan LCQ Deca XP Plus ion trap mass spectrometer or LTQ). MS/MS spectra can be evaluated using, e.g., the program Sequest with the NCBI human protein database.

The methylation sites identified are summarized in Table 1 (SEQ ID NOs: 1-4977) and the acetylation sites identified are summarized in Table 2 (SEQ ID NOs: 4978-5487). For each row, Column B lists the parent (signaling) protein in which the methylation or acetylation site occurs; Column C lists the SwissProt accession number for the human homologue of the identified parent proteins; Column D lists the protein type/classification of the parent protein; Column E identifies the arginine or lysine residue at which methylation occurs (each number refers to the amino acid residue position of the arginine or lysine in the parent human protein, according to the published sequence retrieved by the SwissProt accession number); Column F shows flanking sequences of the identified methylatable arginine or lysine residues (which are the sequences of trypsin-digested peptides). (Note that the SEQ ID NO for the trypsin-digested peptide sequence set forth in Column F is given in Column H); Column G lists the cell line/Tissue type in which methylation or acetylation site was discovered.

One of skill in the art will appreciate that, in many instances the utility of the instant disclosure is best understood in conjunction with an appreciation of the many biological roles and significance of the various target signaling proteins/polypeptides of the disclosure.

The disclosure also features peptides comprising a methylation or acetylation site of the disclosure. In one particular embodiment, the peptides comprise any one of the an amino acid sequences as set forth in column F of Table 1 or Table 2, which are trypsin-digested peptide fragments of the parent proteins. Alternatively, a parent signaling protein listed in Table 1 or Table 2 may be digested with another protease, and the sequence of a peptide fragment comprising a methylation or acetylation site can be obtained in a similar way. Suitable proteases include, but are not limited to, serine proteases (e.g. hepsin), metallo proteases (e.g. PUMP1), chymotrypsin, cathepsin, pepsin, thermolysin, carboxypeptidases, etc.

The disclosure also features proteins and peptides that are mutated to eliminate a methylation or acetylation site of the disclosure. Such proteins and peptides are particular useful as research tools to understand complex signaling transduction pathways of cancer cells, for example, to identify new upstream methylase(s) or demethylase(s) or other proteins that regulates the activity of a signaling protein; to identify downstream effector molecules that interact with a signaling protein, etc.

Various methods that are well known in the art can be used to eliminate a methylation or acetylation site. For example, the methylatable arginine or lysine or acetylatable lysine may be mutated into a non-methylatable or—acetylatable residue, such as glutamine. A "methylatable" amino acid refers to an amino acid that is capable of being modified by addition of a methyl group (and includes both methylated form and unmethylated form). An "acetylatable" amino acid refers to an amino acid that is capable of being modified by addition of a acetyl group (and includes both acetylated form and unacetylated form). Alternatively, the arginine or lysine may be deleted. Residues other than the arginine or lysine may also be modified (e.g., delete or mutated) if such modification inhibits the methylation of the arginine or lysine residue. For example, residues flanking the arginine or lysine may be deleted or mutated, so that a methylase cannot recognize/methylated the mutated protein or the peptide. Standard mutagenesis and molecular cloning techniques can be used to create amino acid substitutions or deletions.

Modulators of the Methylation or Acetylation Sites

In another aspect, the disclosure features a modulator that modulates arginine or lysine methylation at a methylation or acetylation site of the disclosure, including small molecules, peptides comprising a methylation or acetylation site, and binding molecules that specifically bind at a methylation or acetylation site, including but not limited to antibodies or antigen-binding fragments thereof.

Modulators of an methylation or acetylation site include any molecules that directly or indirectly counteract, reduce, antagonize or inhibit arginine or lysine methylation or acetylation of the site. The modulators may compete or block the binding of the to its upstream methylase(s) or demethylase(s), or to its downstream signaling transduction molecule(s).

The modulators may directly interact with a methylation or acetylation site. The modulator may also be a molecule that does not directly interact with a methylation or acetylation site. For example, the modulators can be dominant negative mutants, i.e., proteins and peptides that are mutated to eliminate the methylation or acetylation site. Such mutated proteins or peptides could retain the binding ability to a downstream signaling molecule but lose the ability to trigger downstream signaling transduction of the wild type parent signaling protein.

The modulators include small molecules that modulate the arginine or lysine methylation or acetylation at a methylation or acetylation site of the disclosure. Chemical agents, referred to in the art as "small molecule" compounds are typically organic, non-peptide molecules, having a molecular weight less than 10,000, less than 5,000, less than 1,000, or less than 500 daltons. This class of modulators includes chemically synthesized molecules, for instance, compounds from combinatorial chemical libraries. Synthetic compounds may be rationally designed or identified based on known or inferred properties of a methylation or acetylation site of the disclosure or may be identified by screening compound libraries. Alternative appropriate modulators of this class are natural products, particularly secondary metabolites from organisms such as plants or fungi, which can also be identified by screening compound libraries. Methods for generating and obtaining compounds are well known in the art (Schreiber S L, Science 151: 1964-1969 (2000); Radmann J. and Gunther J., Science 151: 1947-1948 (2000)).

The modulators also include peptidomimetics, small protein-like chains designed to mimic peptides. Peptidomimetics may be analogues of a peptide comprising a methylation or acetylation site of the disclosure. Peptidomimetics may also be analogues of a modified peptide that are mutated to eliminate a methylation or acetylation site of the disclosure. Peptidomimetics (both peptide and non-peptidyl analogues) may have improved properties (e.g., decreased proteolysis, increased retention or increased bioavailability). Peptidomimetics generally have improved oral availability, which makes them especially suited to treatment of disorders in a human or animal.

In certain embodiments, the modulators are peptides comprising a methylation or acetylation site of the disclosure. In certain embodiments, the modulators are antibodies or antigen-binding fragments thereof that specifically bind at a methylation or acetylation site of the disclosure.

Heavy-Isotope Labeled Peptides (AQUA Peptides).

In another aspect, the invention provides peptides comprising a methylation or acetylation site of the invention. In a particular embodiment, the invention provides Heavy-Isotope Labeled Peptides (AQUA peptides) comprising a methylation or acetylation site. Such peptides are useful to generate methylation or acetylation site-specific antibodies for a methylation or acetylation site. Such peptides are also useful as potential diagnostic tools for screening different types of diseases including cancer (e.g., a carcinoma such as colorectal cancer), or as potential therapeutic agents for treating diseases such as carcinomas (e.g., colorectal cancer).

The peptides may be of any length, typically six to fifteen amino acids. The methylation or acetylation site can occur at any position in the peptide; if the peptide will be used as an immunogen, it typically is from seven to twenty amino acids in length. In some embodiments, the peptide is labeled with a detectable marker.

"Heavy-isotope labeled peptide" (used interchangeably with AQUA peptide) refers to a peptide comprising at least one heavy-isotope label, as described in PCT Publication No. WO/03016861, "Absolute Quantification of Proteins and Modified Forms Thereof by Multistage Mass Spectrometry" (Gygi et al.) (the teachings of which are hereby incorporated herein by reference, in their entirety). The amino acid sequence of an AQUA peptide is identical to the sequence of a proteolytic fragment of the parent protein in which the methylation or acetylation site occurs. AQUA peptides of the invention are highly useful for detecting, quantitating or modulating a methylation or acetylation site of the invention (both in methylated and non-methylated forms) in a biological sample.

A peptide of the invention, including an AQUA peptide, comprises any methylation or acetylation site. In some embodiments, the peptide or AQUA peptide comprises a methylation site of a protein in Table 1 or acetylation site of a protein in Table 2 that may be a secreted protein, adaptor/scaffold protein, non-receptor ser/thr protein kinase, non-receptor tyrosine protein kinase, chromatin/DNA binding/repair/replication protein, cytoskeletal protein, mitochondrial protein, transcriptional regulator, translational regulator, ubiquitin conjugating system protein, cell cycle regulation protein, RNA processing protein, adhesion or extracellular matrix protein, proteases, kinases (or regulatory subunit thereof), apoptosis protein, chaperone protein, receptor/channel/transporter/cell surface protein, enzyme, G protein or regulator protein, endoplasmic reticulum or golgi protein, calcium-binding protein, vesicle proteins, motor or contractile protein, non-protein kinase, phosphatase, or a protein of unknown function.

In some embodiments, the peptide or AQUA peptide comprises the amino acid sequence shown in any one of the above listed SEQ ID NOs. In some embodiments, the peptide or AQUA peptide consists of the amino acid sequence in said SEQ ID NOs. In some embodiments, the peptide or AQUA peptide comprises a fragment of the amino acid sequence in said SEQ ID NOs., wherein the fragment is six to twenty amino acids long and includes the methylatable lysine or arginine. In some embodiments, the peptide or AQUA peptide consists of a fragment of the amino acid sequence in said SEQ ID NOs., wherein the fragment is six to twenty amino acids long and includes the methylatable lysine or arginine.

In certain embodiments, the peptide or AQUA peptide comprises any one of the SEQ ID NOs listed in column H, which are trypsin-digested peptide fragments of the parent proteins.

It is understood that parent protein listed in Table 1 or Table 2 may be digested with any suitable protease (e.g., serine proteases (e.g. trypsin, hepsin), metallo proteases (e.g. PUMP1), chymotrypsin, cathepsin, pepsin, thermolysin, carboxypeptidases, etc.), and the resulting peptide sequence comprising a methylatable site of the invention may differ from that of trypsin-digested fragments (as set forth in Column F), depending the cleavage site of a particular enzyme. An AQUA peptide for a particular a parent protein sequence should be chosen based on the amino acid sequence of the parent protein and the particular protease for digestion; that is, the AQUA peptide should match the amino acid sequence of a proteolytic fragment of the parent protein in which the methylation or acetylation site occurs.

An AQUA peptide is typically at least about 6 amino acids long. An exemplary range is about 7 to 15 amino acids in length. A peptide sequence can be selected that is not likely to be chemically reactive during mass spectrometry. For example, sequences comprising cysteine, tryptophan, or methionine can be avoided.

The AQUA method detects and quantifies a target protein in a sample by introducing a known quantity of at least one heavy-isotope labeled peptide standard (which has a unique signature detectable by LC-SRM chromatography) into a digested biological sample. By comparing to the peptide standard, one may readily determine the quantity of a peptide having the same sequence and protein modification(s) in the biological sample. Briefly, the AQUA methodology has two stages: (1) peptide internal standard selection and validation; method development; and (2) implementation using validated peptide internal standards to detect and quantify a target protein in a sample. The method is a powerful technique for detecting and quantifying a given peptide/protein within a complex biological mixture, such as a cell lysate, and may be used, e.g., to quantify change in protein methylation as a result of drug treatment, or to quantify a protein in different biological states.

Generally, to develop a suitable internal standard, a particular peptide (or modified peptide) within a target protein sequence is chosen based on its amino acid sequence and a particular protease for digestion. The peptide is then generated by solid-phase peptide synthesis such that one residue is replaced with that same residue containing stable isotopes ($^{13}C$, $^{15}N$). The result is a peptide that is chemically identical to its native counterpart formed by proteolysis, but is easily distinguishable by MS via a mass shift. A newly synthesized AQUA internal standard peptide is then evaluated by LC-MS/MS. This process provides qualitative information about peptide retention by reverse-phase chromatography, ionization efficiency, and fragmentation via collision-induced dissociation. Informative and abundant fragment ions for sets of native and internal standard peptides are chosen and then specifically monitored in rapid succession as a function of chromatographic retention to form a selected reaction monitoring (LC-SRM) method based on the unique profile of the peptide standard.

The second stage of the AQUA strategy is its implementation to measure the amount of a protein or the modified form of the protein from complex mixtures. Whole cell lysates are typically fractionated by SDS-PAGE gel electrophoresis, and regions of the gel consistent with protein migration are excised. This process is followed by in-gel proteolysis in the presence of the AQUA peptides and LC-SRM analysis. (See Gerber et al. supra.) AQUA peptides are spiked in to the complex peptide mixture obtained by digestion of the whole cell lysate with a proteolytic enzyme and subjected to immunoaffinity purification as described above. The retention time and fragmentation pattern of the native peptide formed by protease digestion (e.g., trypsinization) is identical to that of the AQUA internal standard peptide determined previously; thus, LC-MS/MS analysis using an SRM experiment results in the highly specific and sensitive measurement of both internal standard and analyte directly from extremely complex peptide mixtures. Because an absolute amount of the AQUA peptide is added (e.g. 250 fmol), the ratio of the areas under the curve can be used to determine the precise expression levels of a protein or methylated form of a protein in the original cell lysate. In addition, the internal standard is present during in-gel digestion as native peptides are formed, such that peptide extraction efficiency from gel pieces, absolute losses during sample handling (including vacuum centrifugation), and variability during introduction into the LC-MS system do not affect the determined ratio of native and AQUA peptide abundances.

An AQUA peptide standard may be developed for a known methylation site previously identified by the IAP-LC-MS/MS method within a target protein. One AQUA peptide incorporating the methylated form of the site, and a second AQUA peptide incorporating the non-methylated form of site may be developed. In this way, the two standards may be used to detect and quantify both the methylated and non-methylated forms of the site in a biological sample.

Peptide internal standards may also be generated by examining the primary amino acid sequence of a protein and determining the boundaries of peptides produced by protease cleavage. Alternatively, a protein may actually be digested with a protease and a particular peptide fragment produced can then sequenced. Suitable proteases include, but are not limited to, serine proteases (e.g. trypsin, hepsin), metallo proteases (e.g. PUMP1), chymotrypsin, cathepsin, pepsin, thermolysin, carboxypeptidases, etc.

A peptide sequence that is outside a methylation or acetylation site may be selected as internal standard to determine the quantity of all forms of the target protein. Alternatively, a peptide encompassing a methylated site may be selected as internal standard to detect and quantify only the methylated form of the target protein. Peptide standards for both methylated form and non-methylated form can be used together, to determine the extent of methylation in a particular sample.

The peptide is labeled using one or more labeled amino acids (i.e. the label is an actual part of the peptide) or labels may be attached after synthesis according to standard methods. In some embodiments, the label is a mass-altering label selected based on the following considerations: The mass should be unique to shift fragment masses produced by MS analysis to regions of the spectrum with low background; the ion mass signature component is the portion of the labeling moiety that exhibits a unique ion mass signature in MS analysis; the sum of the masses of the constituent atoms of the label can be uniquely different than the fragments of all the possible amino acids. As a result, the labeled amino acids and peptides are readily distinguished from unlabeled ones by the ion/mass pattern in the resulting mass spectrum. The ion mass signature component can be selected to impart a mass to a protein fragment that does not match the residue mass for any of the 20 natural amino acids.

The label should be robust under the fragmentation conditions of MS and not undergo unfavorable fragmentation. Labeling chemistry can be selected be efficient under a range of conditions, particularly denaturing conditions, and the labeled tag can be selected such that it remains soluble in the MS buffer system of choice. In some embodiments, the label does not suppress the ionization efficiency of the protein and is not chemically reactive. The label may contain a mixture of two or more isotopically distinct species to generate a unique mass spectrometric pattern at each labeled fragment position. Stable isotopes, such as $^{13}C$, $^{15}N$, $^{17}O$, $^{18}O$, or $^{34}S$, are among the exemplary labels that may be used. Pairs of peptide internal standards that incorporate a different isotope label may also be prepared. Exemplary amino acid residues into which a heavy isotope label may be incorporated include leucine, proline, valine, and phenylalanine.

Peptide internal standards can be characterized according to their mass-to-charge (m/z) ratio, and also according to their retention time on a chromatographic column (e.g. an HPLC column). Internal standards that co-elute with unlabeled peptides of identical sequence are selected as optimal internal standards. The internal standard is then analyzed by fragmenting the peptide by any suitable means, for example by collision-induced dissociation (CID) using, e.g., argon or helium as a collision gas. The fragments are then analyzed, for example by multi-stage mass spectrometry (MS") to obtain a fragment ion spectrum, to obtain a peptide fragmentation signature. Peptide fragments can be selected that have significant differences in m/z ratios to enable peaks corresponding to each fragment to be well separated, and a signature that is unique for the target peptide is obtained. If a suitable fragment signature is not obtained at the first stage, additional stages of MS are performed until a unique signature is obtained.

Fragment ions in the MS/MS and $MS^3$ spectra are typically highly specific for the peptide of interest, and, in conjunction with LC methods, allow a highly selective means of detecting and quantifying a target peptide/protein in a complex protein mixture, such as a cell lysate, containing many thousands or tens of thousands of proteins. Any biological sample potentially containing a target protein/peptide of interest may be assayed. Crude or partially purified cell extracts can be used. Generally, the sample has at least 0.01 mg of protein, typically a concentration of 0.1-10 mg/mL, and may be adjusted to a desired buffer concentration and pH.

A known amount of a labeled peptide internal standard, e.g., about 10 femtomoles, corresponding to a target protein to be detected/quantified is then added to a biological sample, such as a cell lysate. The spiked sample is then digested with one or more protease(s) for a suitable time period to allow digestion. A separation is then performed (e.g., by HPLC, reverse-phase HPLC, capillary electrophoresis, ion exchange chromatography, etc.) to isolate the labeled internal standard and its corresponding target peptide from other peptides in the sample. Microcapillary LC is an exemplary method.

Each isolated peptide is then examined by monitoring of a selected reaction in the MS. This involves using the prior knowledge gained by the characterization of the peptide internal standard and then requiring the MS to continuously monitor a specific ion in the MS/MS or MS" spectrum for both the peptide of interest and the internal standard. After elution, the area under the curve (AUC) for both peptide standard and target peptide peaks are calculated. The ratio of the two areas provides the absolute quantification that can be normalized for the number of cells used in the analysis and the protein's molecular weight, to provide the precise number of copies of the protein per cell. Further details of the AQUA methodology are described in Gygi et al., PCT Publication No. WO/03016861, and Gerber et al., *Proc. Natl. Acad. Sci. U.S.A.* 100: 6940-5 (2003), both of which are hereby incorporated by reference in their entirety.

Accordingly, AQUA internal peptide standards (heavy-isotope labeled peptides) may be produced, as described above, for any of the methylation sites of the invention (see Table 1) or acetylation sites of the invention (see Table 2). For example, peptide standards for a given methylation or acetylation site may be produced for both the methylated and non-methylated forms of the sequence. Such standards may be used to detect and quantify both methylated form and non-methylated form of the parent protein in a biological sample.

Heavy-isotope labeled equivalents of a methylation or acetylation site of the disclosure, both in methylated and non-methylated form, can be readily synthesized and their unique MS and LC-SRM signature determined, so that the peptides are validated as AQUA peptides and ready for use in quantification.

The methylation or acetylation sites of the invention are particularly well suited for development of corresponding AQUA peptides, since the IAP method by which they were identified inherently confirmed that such peptides are in fact produced by enzymatic digestion (e.g., trypsinization) and are in fact suitably fractionated/ionized in MS/MS. Thus, heavy-isotope labeled equivalents of these peptides (both in methylated and non-methylated form) can be readily synthesized and their unique MS and LC-SRM signature determined, so that the peptides are validated as AQUA peptides and ready for use in quantification experiments.

Peptides and AQUA peptides provided by the invention will be highly useful in the further study of signal transduction anomalies underlying cancer, including carcinomas. Peptides and AQUA peptides of the invention may also be used for identifying diagnostic/bio-markers of carcinomas, identifying new potential drug targets, and/or monitoring the effects of test therapeutic agents on signaling proteins and pathways.

Methylation or Acetylation Site-Specific Antibodies

In another aspect, the disclosure discloses methylation or acetylation site-specific binding molecules that specifically bind at a arginine or lysine methylation or acetylation site of the disclosure, and that distinguish between the methylated and unmethylated forms. In one embodiment, the binding molecule is an antibody or an antigen-binding fragment thereof. The antibody may specifically bind to an amino acid sequence comprising a methylation site identified in Table 1 or acetylation site identified in Table 2.

In some embodiments, the antibody or antigen-binding fragment thereof specifically binds the methylated or acetylated site. In other embodiments, the antibody or antigen-binding fragment thereof specially binds the unmethylated or unacetylated site. An antibody or antigen-binding fragment thereof specially binds an amino acid sequence comprising an arginine or lysine methylation site in Table 1 or a lysine acetylation site in Table 2 when it does not significantly bind any other site in the parent protein and does not significantly bind a protein other than the parent protein. An antibody of the disclosure is sometimes referred to herein as a "methyl-specific" or "acetyl-specific" antibody, e.g., a methyl-arginine specific antibody or a methyl-lysine specific antibody.

An antibody or antigen-binding fragment thereof specially binds an antigen when the dissociation constant is ≤1 mM, e.g., ≤100 nM or ≤10 nM.

In some embodiments, the antibody or antigen-binding fragment of the disclosure binds an amino acid sequence that comprises a methylation site of a protein in Table 1 or acetylation site of a protein in Table 2 that is a secreted protein, adaptor/scaffold protein, non-receptor ser/thr protein kinase, non-receptor tyrosine protein kinase, chromatin/DNA binding/repair/replication protein, cytoskeletal protein, mitochondrial protein, transcriptional regulator, translational regulator, cell cycle regulation protein, RNA processing protein, adhesion or extracellular matrix protein, proteases, kinases (or regulatory subunit thereof), apoptosis protein, chaperone protein, receptor/channel/transporter/cell surface protein, enzyme, G protein or regulator protein, endoplasmic reticulum or golgi protein, calcium-binding protein, vesicle proteins, motor or contractile protein, non-protein kinase, phosphatase, or a protein of unknown function.

In some embodiments, an antibody or antigen-binding fragment thereof of the disclosure specifically binds an amino acid sequence comprising any one of the above listed SEQ ID NOs. In some embodiments, an antibody or antigen-binding fragment thereof of the disclosure especially binds an amino acid sequence comprises a fragment of one of said SEQ ID NOs., wherein the fragment is four to twenty amino acid long and includes the methylatable arginine or lysine.

In certain embodiments, an antibody or antigen-binding fragment thereof of the disclosure specially binds an amino acid sequence that comprises a peptide produced by proteolysis of the parent protein with a protease wherein said peptide comprises a arginine or lysine methylation or acetylation site of the disclosure. In some embodiments, the peptides are produced from trypsin digestion of the parent protein. The parent protein comprising the arginine or lysine methylation or acetylation site can be from any species, e.g., from a mammal including but not limited to non-human primates, rabbits, mice, rats, goats, cows, sheep, and guinea pigs. In some embodiments, the parent protein is a human protein and the antibody binds an epitope comprising the arginine or lysine methylation shown by a lower case "k" or "r" Column F of Table 1 or acetylation site shown by a lower case "k" in Column F of Table 2. Such peptides include any one of the SEQ ID NOs.

An antibody of the disclosure can be an intact, four immunoglobulin chain antibody comprising two heavy chains and two light chains. The heavy chain of the antibody can be of any isotype including IgM, IgG, IgE, IgG, IgA or IgD or sub-isotype including IgG1, IgG2, IgG3, IgG4, IgE1, IgE2, etc. The light chain can be a kappa light chain or a lambda light chain.

Also within the disclosure are antibody molecules with fewer than 4 chains, including single chain antibodies, Camelid antibodies and the like and components of the antibody, including a heavy chain or a light chain. The term "antibody" (or "antibodies") refers to all types of immunoglobulins. The term "an antigen-binding fragment of an antibody" refers to any portion of an antibody that retains specific binding of the intact antibody. An exemplary antigen-binding fragment of an antibody is the heavy chain and/or light chain CDR, or the heavy and/or light chain variable region. The term "does not bind," when appeared in context of an antibody's binding to one methyl-form (e.g., methylated form) of a sequence, means that the antibody does not substantially react with the other methyl-form (e.g., non-methylated form) of the same sequence. One of skill in the art will appreciate that the expression may be applicable in those instances when (1) an methyl-specific antibody either does not apparently bind to the non-methyl form of the antigen as ascertained in commonly used experimental detection systems (Western blotting, IHC, Immunofluorescence, etc.); (2) where there is some reactivity with the surrounding amino acid sequence, but that the methylated residue is an immunodominant feature of the reaction. In cases such as these, there is an apparent difference in affinities for the two sequences. Dilutional analyses of such antibodies indicates that the antibodies apparent affinity for the methylated form is at least 10-100 fold higher than for the non-methylated form; or where (3) the methyl-specific antibody reacts no more than an appropriate control antibody would react under identical experimental conditions. A control antibody preparation might be, for instance, purified immunoglobulin from a pre-immune animal of the same species, an isotype- and species-matched monoclonal antibody. Tests using control antibodies to demonstrate specificity are recognized by one of skill in the art as appropriate and definitive.

In some embodiments an immunoglobulin chain may comprise in order from 5' to 3', a variable region and a constant region. The variable region may comprise three complementarity determining regions (CDRs), with interspersed framework (FR) regions for a structure FR1, CDR1, FR2, CDR2, FR3, CDR3 and FR4. Also within the disclosure are heavy or light chain variable regions, framework regions and CDRs. An antibody of the disclosure may comprise a heavy chain constant region that comprises some or all of a CH1 region, hinge, CH2 and CH3 region.

An antibody of the disclosure may have an binding affinity ($K_D$) of $1\times10^{-7}$ M or less. In other embodiments, the antibody binds with a $K_D$ of $1\times10^{-8}$ M, $1\times10^{-9}$ M, $1\times10^{-10}$ M, $1\times10^{-11}$ M, $1\times10^{-12}$ M or less. In certain embodiments, the $K_D$ is 1 pM to 500 pM, between 500 pM to 1 μM, between 1 μM to 100 nM, or between 100 mM to 10 nM.

Antibodies of the disclosure can be derived from any species of animal, e.g., a mammal. Non-limiting exemplary natural antibodies include antibodies derived from human, chicken, goats, and rodents (e.g., rats, mice, hamsters and rabbits), including transgenic rodents genetically engineered to produce human antibodies (see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety). Natural antibodies are the antibodies produced by a host animal. "Genetically altered antibodies" refer to antibodies wherein the amino acid sequence has been varied from that of a native antibody. Because of the relevance of recombinant DNA techniques to this application, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics.

The antibodies of the disclosure include antibodies of any isotype including IgM, IgG, IgD, IgA and IgE, and any sub-isotype, including IgG1, IgG2a, IgG2b, IgG3 and IgG4, IgE1, IgE2 etc. The light chains of the antibodies can either be kappa light chains or lambda light chains.

Antibodies disclosed in the disclosure may be polyclonal or monoclonal. As used herein, the term "epitope" refers to the smallest portion of a protein capable of selectively binding to the antigen binding site of an antibody. It is well accepted by those skilled in the art that the minimal size of a protein epitope capable of selectively binding to the antigen binding site of an antibody is about five or six to seven amino acids.

Other antibodies specifically contemplated are oligoclonal antibodies. As used herein, the phrase "oligoclonal antibodies" refers to a predetermined mixture of distinct monoclonal antibodies. See, e.g., PCT publication WO 95/20401; U.S. Pat. Nos. 5,789,208 and 6,335,163. In one embodiment, oligoclonal antibodies consisting of a predetermined mixture of antibodies against one or more epitopes are generated in a single cell. In other embodiments, oligoclonal antibodies comprise a plurality of heavy chains capable of pairing with a common light chain to generate antibodies with multiple specificities (e.g., PCT publication WO 04/009618). Oligoclonal antibodies are particularly useful when it is desired to target multiple epitopes on a single target molecule. In view of the assays and epitopes disclosed herein, those skilled in the art can generate or select antibodies or mixtures of antibodies that are applicable for an intended purpose and desired need.

Recombinant antibodies against the methylation or acetylation sites identified in the disclosure are also included in the present application. These recombinant antibodies have the same amino acid sequence as the natural antibodies or have altered amino acid sequences of the natural antibodies in the present application. They can be made in any expression systems including both prokaryotic and eukaryotic expression systems or using phage display methods (see, e.g., Dower et al., WO91/17271 and McCafferty et al., WO92/01047; U.S. Pat. No. 5,969,108, which are herein incorporated by reference in their entirety).

Antibodies can be engineered in numerous ways. They can be made as single-chain antibodies (including small modular immunopharmaceuticals or SMIPs™), Fab and F(ab')$_2$ fragments, etc. Antibodies can be humanized, chimerized, deimmunized, or fully human. Numerous publications set forth the many types of antibodies and the methods of engineering such antibodies. For example, see U.S. Pat. Nos. 6,355,245; 6,180,370; 5,693,762; 6,407,213; 6,548,640; 5,565,332; 5,225,539; 6,103,889; and 5,260,203.

The genetically altered antibodies should be functionally equivalent to the above-mentioned natural antibodies. In certain embodiments, modified antibodies provide improved stability or/and therapeutic efficacy. Examples of modified antibodies include those with conservative substitutions of amino acid residues, and one or more deletions or additions of amino acids that do not significantly deleteriously alter the antigen binding utility. Substitutions can range from changing or modifying one or more amino acid residues to complete redesign of a region as long as the therapeutic utility is maintained. Antibodies of this application can be modified post-translationally (e.g., phosphorylation, and/or methylation) or can be modified synthetically (e.g., the attachment of a labeling group).

Antibodies with engineered or variant constant or Fc regions can be useful in modulating effector functions, such as, for example, antigen-dependent cytotoxicity (ADCC) and complement-dependent cytotoxicity (CDC). Such antibodies with engineered or variant constant or Fc regions may be useful in instances where a parent singling protein (Table 1 or Table 2) is expressed in normal tissue; variant antibodies without effector function in these instances may elicit the desired therapeutic response while not damaging normal tissue. Accordingly, certain aspects and methods of the present disclosure relate to antibodies with altered effector functions that comprise one or more amino acid substitutions, insertions, and/or deletions.

In certain embodiments, genetically altered antibodies are chimeric antibodies and humanized antibodies.

The chimeric antibody is an antibody having portions derived from different antibodies. For example, a chimeric antibody may have a variable region and a constant region derived from two different antibodies. The donor antibodies may be from different species. In certain embodiments, the variable region of a chimeric antibody is non-human, e.g., murine, and the constant region is human.

The genetically altered antibodies used in the disclosure include CDR grafted humanized antibodies. In one embodiment, the humanized antibody comprises heavy and/or light chain CDRs of a non-human donor immunoglobulin and heavy chain and light chain frameworks and constant regions of a human acceptor immunoglobulin. The method of making humanized antibody is disclosed in U.S. Pat. Nos. 5,530,101; 5,585,089; 5,693,761; 5,693,762; and 6,180,370 each of which is incorporated herein by reference in its entirety.

Antigen-binding fragments of the antibodies of the disclosure, which retain the binding specificity of the intact antibody, are also included in the disclosure. Examples of these antigen-binding fragments include, but are not limited to, partial or full heavy chains or light chains, variable regions, or CDR regions of any methylation or acetylation site-specific antibodies described herein.

In one embodiment of the disclosure, the antibody fragments are truncated chains (truncated at the carboxyl end). In certain embodiments, these truncated chains possess one or more immunoglobulin activities (e.g., complement fixation activity). Examples of truncated chains include, but are not limited to, Fab fragments (consisting of the VL, VH, CL and CH1 domains); Fd fragments (consisting of the VH and CH1 domains); Fv fragments (consisting of VL and VH domains of a single chain of an antibody); dAb fragments (consisting of a VH domain); isolated CDR regions; (Fab')$_2$ fragments, bivalent fragments (comprising two Fab fragments linked by a disulphide bridge at the hinge region). The truncated chains can be produced by conventional biochemical techniques, such as enzyme cleavage, or recombinant DNA techniques, each of which is known in the art. These polypeptide fragments may be produced by proteolytic cleavage of intact antibodies by methods well known in the art, or by inserting stop codons at the desired locations in the vectors using site-directed mutagenesis, such as after CH1 to produce Fab fragments or after the hinge region to produce (Fab')$_2$ fragments. Single chain antibodies may be produced by joining VL- and VH-coding regions with a DNA that encodes a peptide linker connecting the VL and VH protein fragments Papain digestion of antibodies produces two identical antigen-binding fragments, called "Fab" fragments, each with a single antigen-binding site, and a residual "Fc" fragment, whose name reflects its ability to crystallize readily. Pepsin treatment of an antibody yields an F(ab')$_2$ fragment that has two antigen-combining sites and is still capable of cross-linking antigen.

"Fv" usually refers to the minimum antibody fragment that contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the CDRs confer antigen-binding specificity to the antibody. However, even a single variable domain (or half of an Fv comprising three CDRs specific for an antigen) has the ability to recognize and bind antigen, although likely at a lower affinity than the entire binding site.

Thus, in certain embodiments, the antibodies of the application may comprise 1, 2, 3, 4, 5, 6, or more CDRs that recognize the methylation sites identified in Column F of Table 1 or acetylation sites identified in Column F of Table 2.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

"Single-chain Fv" or "scFv" antibody fragments comprise the $V_H$ and $V_L$ domains of an antibody, wherein these domains are present in a single polypeptide chain. In certain embodiments, the Fv polypeptide further comprises a polypeptide linker between the $V_H$ and $V_L$ domains that enables the scFv to form the desired structure for antigen binding. For a review of scFv see Pluckthun in The Pharmacology of Monoclonal Antibodies, vol. 113, Rosenburg and Moore, eds. (Springer-Verlag: New York, 1994), pp. 269-315.

SMIPs are a class of single-chain peptides engineered to include a target binding region and effector domain (CH2 and CH3 domains). See, e.g., U.S. Patent Application Publication No. 20050238646. The target binding region may be derived from the variable region or CDRs of an antibody, e.g., a methylation or acetylation site-specific antibody of the application. Alternatively, the target binding region is derived from a protein that binds a methylation or acetylation site.

Bispecific antibodies may be monoclonal, human or humanized antibodies that have binding specificities for at least two different antigens. In the present case, one of the binding specificities is for the methylation or acetylation site, the other one is for any other antigen, such as for example, a cell-surface protein or receptor or receptor subunit. Alternatively, a therapeutic agent may be placed on one arm. The therapeutic agent can be a drug, toxin, enzyme, DNA, radionuclide, etc.

In some embodiments, the antigen-binding fragment can be a diabody. The term "diabody" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90: 6444-6448 (1993).

Camelid antibodies refer to a unique type of antibodies that are devoid of light chain, initially discovered from animals of the camelid family. The heavy chains of these so-called heavy-chain antibodies bind their antigen by one single domain, the variable domain of the heavy immunoglobulin chain, referred to as VHH. VHHs show homology with the variable domain of heavy chains of the human VHIII family. The VHHs obtained from an immunized camel, dromedary, or llama have a number of advantages, such as effective production in microorganisms such as *Saccharomyces cerevisiae*.

In certain embodiments, single chain antibodies, and chimeric, humanized or primatized (CDR-grafted) antibodies, as well as chimeric or CDR-grafted single chain antibodies, comprising portions derived from different species, are also encompassed by the present disclosure as antigen-binding fragments of an antibody. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., U.S. Pat. Nos. 4,816,567 and 6,331,415; U.S. Pat. No. 4,816,397; European Patent No. 0,120,694; WO 86/01533; European Patent No. 0,194,276 B1; U.S. Pat. No. 5,225,539; and European Patent No. 0,239,400 B1. See also, Newman et al., BioTechnology, 10: 1455-1460 (1992), regarding primatized antibody. See, e.g., Ladner et al., U.S. Pat. No. 4,946,778; and Bird et al., Science, 242: 423-426 (1988)), regarding single chain antibodies.

In addition, functional fragments of antibodies, including fragments of chimeric, humanized, primatized or single chain antibodies, can also be produced. Functional fragments of the subject antibodies retain at least one binding function and/or modulation function of the full-length antibody from which they are derived.

Since the immunoglobulin-related genes contain separate functional regions, each having one or more distinct biological activities, the genes of the antibody fragments may be fused to functional regions from other genes (e.g., enzymes, U.S. Pat. No. 5,004,692, which is incorporated by reference in its entirety) to produce fusion proteins or conjugates having properties.

Non-immunoglobulin binding polypeptides are also contemplated. For example, CDRs from an antibody disclosed herein may be inserted into a suitable non-immunoglobulin scaffold to create a non-immunoglobulin binding polypeptide. Suitable candidate scaffold structures may be derived from, for example, members of fibronectin type III and cadherin superfamilies.

Also contemplated are other equivalent non-antibody molecules, such as protein binding domains or aptamers, which bind, in a methyl-specific or acetyl-specific manner, to an amino acid sequence comprising a methylation or acetylation site of the disclosure. See, e.g., Neuberger et al., Nature 312: 604 (1984). Aptamers are oligonucleic acid or peptide molecules that bind a specific target molecule. DNA or RNA aptamers are typically short oligonucleotides, engineered through repeated rounds of selection to bind to a molecular target. Peptide aptamers typically consist of a variable peptide loop attached at both ends to a protein scaffold. This double structural constraint generally increases the binding affinity of the peptide aptamer to levels comparable to an antibody (nanomolar range).

The disclosure also discloses the use of the methylation or acetylation site-specific antibodies with immunotoxins. Conjugates that are immunotoxins including antibodies have been widely described in the art. The toxins may be coupled to the antibodies by conventional coupling techniques or immunotoxins containing protein toxin portions can be produced as fusion proteins. In certain embodiments, antibody conjugates may comprise stable linkers and may release cytotoxic agents inside cells (see U.S. Pat. Nos. 6,867,007 and 6,884,869). The conjugates of the present application can be used in a corresponding way to obtain such immunotoxins. Illustrative of such immunotoxins are those described by Byers et al., Seminars Cell Biol 2:59-70 (1991) and by Fanger et al., Immunol Today 12:51-54 (1991). Exemplary immunotoxins include radiotherapeutic agents, ribosome-inactivating proteins (RIPs), chemotherapeutic agents, toxic peptides, or toxic proteins.

The methylation or acetylation site-specific antibodies disclosed in the disclosure may be used singly or in combination. The antibodies may also be used in an array format for high throughput uses. An antibody microarray is a collection of immobolized antibodies, typically spotted and fixed on a solid surface (such as glass, plastic and silicon chip).

In another aspect, the antibodies of the disclosure modulate at least one, or all, biological activities of a parent protein identified in Column B of Table 1 or Table 2. The biological activities of a parent protein identified in Column B of Table 1 or Table 2 include: 1) ligand binding activities (for instance, these neutralizing antibodies may be capable of competing with or completely blocking the binding of a parent signaling protein to at least one, or all, of its ligands; 2) signaling transduction activities, such as receptor dimerization, or arginine or lysine methylation; and 3) cellular responses induced by a parent signaling protein, such as oncogenic activities (e.g., cancer cell proliferation mediated by a parent signaling protein), and/or angiogenic activities.

In certain embodiments, the antibodies of the disclosure may have at least one activity selected from the group consisting of: 1) inhibiting cancer cell growth or proliferation; 2) inhibiting cancer cell survival; 3) inhibiting angiogenesis; 4) inhibiting cancer cell metastasis, adhesion, migration or invasion; 5) inducing apoptosis of cancer cells; 6) incorporating a toxic conjugate; and 7) acting as a diagnostic marker.

In certain embodiments, the methylation or acetylation site specific antibodies disclosed in the disclosure are especially indicated for diagnostic and therapeutic applications as described herein. Accordingly, the antibodies may be used in therapies, including combination therapies, in the diagnosis and prognosis of disease, as well as in the monitoring of disease progression. The disclosure, thus, further includes compositions comprising one or more embodiments of an antibody or an antigen binding portion of the disclosure as described herein. The composition may further comprise a pharmaceutically acceptable carrier. The composition may comprise two or more antibodies or antigen-binding portions, each with specificity for a different arginine or lysine methylation or acetylation site of the disclosure or two or more different antibodies or antigen-binding portions all of which are specific for the same arginine or lysine methylation or acetylation site of the disclosure. A composition of the disclosure may comprise one or more antibodies or antigen-binding portions of the disclosure and one or more additional reagents, diagnostic agents or therapeutic agents.

The present application provides for the polynucleotide molecules encoding the antibodies and antibody fragments and their analogs described herein. Because of the degeneracy of the genetic code, a variety of nucleic acid sequences encode each antibody amino acid sequence. The desired nucleic acid sequences can be produced by de novo solid-phase DNA synthesis or by PCR mutagenesis of an earlier prepared variant of the desired polynucleotide. In one embodiment, the codons that are used comprise those that are typical for human or mouse (see, e.g., Nakamura, Y., Nucleic Acids Res. 28: 292 (2000)).

The disclosure also features immortalized cell lines that produce an antibody of the disclosure. For example, hybridoma clones, constructed as described above, that produce monoclonal antibodies to the targeted signaling protein methylation sties disclosed herein are also provided. Similarly, the disclosure includes recombinant cells producing an antibody of the disclosure, which cells may be constructed by well known techniques; for example the antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.)

Methods of Making Methylation or Acetylation Site-Specific Antibodies

In another aspect, the disclosure features a method for making methylation or acetylation site-specific antibodies.

Polyclonal antibodies of the disclosure may be produced according to standard techniques by immunizing a suitable animal (e.g., rabbit, goat, etc.) with an antigen comprising a arginine and/or lysine methylation or acetylation site of the disclosure. (i.e. a methylation shown in Table 1 or acetylation site shown in Table 2) in either the methylated or unmethylated state, depending upon the desired specificity of the antibody, collecting immune serum from the animal, and separating the polyclonal antibodies from the immune serum, in accordance with known procedures and screening and isolating a polyclonal antibody specific for the arginine or lysine methylation or acetylation site of interest as further described below. Methods for immunizing non-human animals such as mice, rats, sheep, goats, pigs, cattle and horses are well known in the art. See, e.g., Harlow and Lane, *Antibodies: A Laboratory Manual*, New York: Cold Spring Harbor Press, 1990.

The immunogen may be the full length protein or a peptide comprising the arginine or lysine methylation or acetylation site of interest. In some embodiments the immunogen is a peptide of from 7 to 20 amino acids in length, e.g., about 8 to 17 amino acids in length. In some embodiments, the peptide antigen will comprise about 3 to 8 amino acids on each side of the phosphorylatable arginine or lysine. In yet other embodiments, the peptide antigen desirably will comprise four or more amino acids flanking each side of the phosphorylatable amino acid and encompassing it. Peptide antigens suitable for producing antibodies of the disclosure may be designed, constructed and employed in accordance with well-known techniques. See, e.g., Antibodies: A Laboratory Manual, Chapter 5, p. 75-76, Harlow & Lane Eds., Cold Spring Harbor Laboratory (1988); Czernik, *Methods In Enzymology*, 201: 264-283 (1991); Merrifield, *J. Am. Chem. Soc.* 85: 21-49 (1962)).

Suitable peptide antigens may comprise all or partial sequence of a trypsin-digested fragment as set forth in Column F of Table 1 or Table 2. Suitable peptide antigens may also comprise all or partial sequence of a peptide fragment produced by another protease digestion.

Exemplary immunogens are those that comprise a methylation site of a protein in Table 1 or acetylation site of a protein in Table 2 that is a secreted protein, adaptor/scaffold protein, non-receptor ser/thr protein kinase, non-receptor tyrosine protein kinase, chromatin/DNA binding/repair/replication protein, cytoskeletal protein, mitochondrial protein, transcriptional regulator, translational regulator, cell cycle regulation protein, RNA processing protein, adhesion or extracellular matrix protein, proteases, kinases (or regulatory subunit thereof), apoptosis protein, chaperone protein, receptor/channel/transporter/cell surface protein, enzyme, G protein or regulator protein, endoplasmic reticulum or golgi protein, calcium-binding protein, vesicle proteins, motor or contractile protein, non-protein kinase, phosphatase, or a protein of unknown function.

In some embodiments the immunogen is administered with an adjuvant. Suitable adjuvants will be well known to those of skill in the art. Exemplary adjuvants include complete or incomplete Freund's adjuvant, RIBI (muramyl dipeptides) or ISCOM (immunostimulating complexes).

When the above-described methods are used for producing polyclonal antibodies, following immunization, the polyclonal antibodies which secreted into the bloodstream can be recovered using known techniques. Purified forms of these antibodies can, of course, be readily prepared by standard purification techniques, such as for example, affinity chromatography with Protein A, anti-immunoglobulin, or the antigen itself. In any case, in order to monitor the success of immunization, the antibody levels with respect to the antigen in serum will be monitored using standard techniques such as ELISA, RIA and the like.

Monoclonal antibodies of the disclosure may be produced by any of a number of means that are well-known in the art. In some embodiments, antibody-producing B cells are isolated from an animal immunized with a peptide antigen as described above. The B cells may be from the spleen, lymph nodes or peripheral blood. Individual B cells are isolated and screened as described below to identify cells producing an antibody specific for the arginine or lysine methylation or acetylation site of interest. Identified cells are then cultured to produce a monoclonal antibody of the disclosure.

Alternatively, a monoclonal methylation or acetylation site-specific antibody of the disclosure may be produced using standard hybridoma technology, in a hybridoma cell line according to the well-known technique of Kohler and Milstein. See *Nature* 265: 495-97 (1975); Kohler and Milstein, *Eur. J. Immunol.* 6: 511 (1976); see also, Current Protocols in Molecular Biology, Ausubel et al. Eds. (1989). Monoclonal antibodies so produced are highly specific, and improve the selectivity and specificity of diagnostic assay methods provided by the disclosure. For example, a solution containing the appropriate antigen may be injected into a mouse or other species and, after a sufficient time (in keeping with conventional techniques), the animal is sacrificed and spleen cells obtained. The spleen cells are then immortalized by any of a number of standard means. Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene. See, e.g., Harlow and Lane, supra. If fusion with myeloma cells is used, the myeloma cells preferably do not secrete immunoglobulin polypeptides (a non-secretory cell line). Typically the antibody producing cell and the immortalized cell (such as but not limited to myeloma cells) with which it is fused are from the same species. Rabbit fusion hybridomas, for example, may be produced as described in U.S. Pat. No. 5,675,063. The immortalized antibody producing cells, such as hybridoma cells, are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

The disclosure also encompasses antibody-producing cells and cell lines, such as hybridomas, as described above.

Polyclonal or monoclonal antibodies may also be obtained through in vitro immunization. For example, phage display techniques can be used to provide libraries containing a repertoire of antibodies with varying affinities for a particular antigen. Techniques for the identification of high affinity human antibodies from such libraries are described by Griffiths et al., (1994) *EMBO J.*, 13:3245-3260; Nissim et al., ibid, pp. 692-698 and by Griffiths et al., ibid, 12:725-734, which are incorporated by reference.

The antibodies may be produced recombinantly using methods well known in the art for example, according to the methods disclosed in U.S. Pat. No. 4,349,893 (Reading) or U.S. Pat. No. 4,816,567 (Cabilly et al.) The antibodies may also be chemically constructed by specific antibodies made according to the method disclosed in U.S. Pat. No. 4,676,980 (Segel et al.)

Once a desired methylation or acetylation site-specific antibody is identified, polynucleotides encoding the antibody, such as heavy, light chains or both (or single chains in the case of a single chain antibody) or portions thereof such as those encoding the variable region, may be cloned and isolated from antibody-producing cells using means that are well known in the art. For example, the antigen combining site of the monoclonal antibody can be cloned by PCR and single-chain antibodies produced as phage-displayed recombinant antibodies or soluble antibodies in E. coli (see, e.g., Antibody Engineering Protocols, 1995, Humana Press, Sudhir Paul editor.)

Accordingly, in a further aspect, the disclosure features such nucleic acids encoding the heavy chain, the light chain, a variable region, a framework region or a CDR of an antibody of the disclosure. In some embodiments, the nucleic acids are operably linked to expression control sequences. The disclosure, thus, also features vectors and expression control sequences useful for the recombinant expression of an antibody or antigen-binding portion thereof of the disclosure. Those of skill in the art will be able to choose vectors and expression systems that are suitable for the host cell in which the antibody or antigen-binding portion is to be expressed.

Monoclonal antibodies of the disclosure may be produced recombinantly by expressing the encoding nucleic acids in a suitable host cell under suitable conditions. Accordingly, the disclosure further features host cells comprising the nucleic acids and vectors described above.

Monoclonal Fab fragments may also be produced in *Escherichia coli* by recombinant techniques known to those skilled in the art. See, e.g., W. Huse, *Science* 246: 1275-81 (1989); Mullinax et al., *Proc. Nat'l Acad. Sci.* 87: 8095 (1990).

If monoclonal antibodies of a single desired isotype are desired for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.,* 82: 8653 (1985); Spira et al., *J. Immunol. Methods,* 74: 307 (1984)). Alternatively, the isotype of a monoclonal antibody with desirable propertied can be changed using antibody engineering techniques that are well-known in the art.

Methylation or acetylation site-specific antibodies of the disclosure, whether polyclonal or monoclonal, may be screened for epitope and methyl or acetyl-specificity according to standard techniques. See, e.g., Czernik et al., *Methods in Enzymology,* 201: 264-283 (1991). For example, the antibodies may be screened against the methylated and/or unmethylated peptide library by ELISA to ensure specificity for both the desired antigen (i.e. that epitope including an methylation or acetylation site of the disclosure and for reactivity only with the methylated (or unmethylated) form of the antigen. Peptide competition assays may be carried out to confirm lack of reactivity with other methyl-epitopes on the parent protein. The antibodies may also be tested by Western blotting against cell preparations containing the parent signaling protein, e.g., cell lines over-expressing the parent protein, to confirm reactivity with the desired methylated or acetylated epitope/target.

Specificity against the desired methylated epitope may also be examined by constructing mutants lacking methylatable residues at positions outside the desired epitope that are known to be methylated, or by mutating the desired methyl-epitope and confirming lack of reactivity. Methylation or acetylation site-specific antibodies of the disclosure may exhibit some limited cross-reactivity to related epitopes in non-target proteins. This is not unexpected as most antibodies exhibit some degree of cross-reactivity, and anti-peptide antibodies will often cross-react with epitopes having high homology to the immunizing peptide. See, e.g., Czernik, supra. Cross-reactivity with non-target proteins is readily characterized by Western blotting alongside markers of known molecular weight. Amino acid sequences of cross-reacting proteins may be examined to identify methylation or acetylation sites with flanking sequences that are highly homologous to that of a methylation or acetylation site of the disclosure.

In certain cases, polyclonal antisera may exhibit some undesirable general cross-reactivity to methyl-lysine, methyl-arginine, or acetyl-lysine itself, which may be removed by further purification of antisera, e.g., over a methyl-lysine, methyl-arginine, or acetyl-lysine column. Antibodies of the disclosure specifically bind their target protein (i.e. a protein listed in Column B of Table 1 or Table 2) only when methylated or acetylated (or only when not methylated or not acetylated, as the case may be) at the site disclosed in corresponding Columns E/F, and do not (substantially) bind to the other form (as compared to the form for which the antibody is specific).

Antibodies may be further characterized via immunohistochemical (IHC) staining using normal and diseased tissues to examine methylation and activation state and level of a methylation or acetylation site in diseased tissue. IHC may be carried out according to well-known techniques. See, e.g., Antibodies: A Laboratory Manual, Chapter 10, Harlow & Lane Eds., Cold Spring Harbor Laboratory (1988). Briefly, paraffin-embedded tissue (e.g., tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

Antibodies may be further characterized by flow cytometry carried out according to standard methods. See Chow et al., *Cytometry (Communications in Clinical Cytometry)* 46: 72-78 (2001). Briefly and by way of example, the following protocol for cytometric analysis may be employed: samples may be centrifuged on Ficoll gradients to remove lysed erythrocytes and cell debris. Adherring cells may be scrapped off plates and washed with PBS. Cells may then be fixed with 2% paraformaldehyde for 10 minutes at 37° C. followed by permeabilization in 90% methanol for 30 minutes on ice. Cells may then be stained with the primary methylation or acetylation site-specific antibody of the disclosure (which detects a parent signaling protein enumerated in Table 1 or Table 2), washed and labeled with a fluorescent-labeled secondary antibody. Additional fluorochrome-conjugated marker antibodies (e.g., CD45, CD34) may also be added at this time to aid in the subsequent identification of specific hematopoietic cell types. The cells would then be analyzed on a flow cytometer (e.g. a Beckman Coulter FC500) according to the specific protocols of the instrument used.

Antibodies of the disclosure may also be advantageously conjugated to fluorescent dyes (e.g. Alexa488, PE) for use in multi-parametric analyses along with other signal transduction (phospho-CrkL, phospho-Erk 1/2) and/or cell marker (CD34) antibodies.

Methylation or acetylation site-specific antibodies of the disclosure may specifically bind to a signaling protein or polypeptide listed in Table 1 only when methylated or to a signaling protein or polypeptide listed in Table 2 only when acetylated at the specified arginine or lysine residue, but are not limited only to binding to the listed signaling proteins of human species, per se. The disclosure includes antibodies that also bind conserved and highly homologous or identical methylation or acetylation sites in respective signaling proteins from other species (e.g., mouse, rat, monkey, yeast), in addition to binding the methylation or acetylation site of the human homologue. The term "homologous" refers to two or more sequences or subsequences that have at least about 85%, at least 90%, at least 95%, or higher nucleotide or amino acid residue identity, when compared and aligned for maximum correspondence, as measured using sequence comparison method (e.g., BLAST) and/or by visual inspection. Highly homologous or identical sites conserved in other species can readily be identified by standard sequence comparisons (such as BLAST).

Methods for making bispecific antibodies are within the purview of those skilled in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Antibody variable domains with the desired binding specificities (antibody-antigen combining sites) can be fused to immunoglobulin constant domain sequences. In certain embodiments, the fusion is with an immunoglobulin heavy-chain constant domain, including at least part of the hinge, CH2, and CH3 regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, for example, Suresh et al., Methods in Enzymology, 121:210 (1986); WO 96/27011; Brennan et al., Science 229:81 (1985); Shalaby et al., J. Exp. Med. 175:217-225 (1992); Kostelny et al., J. Immunol. 148(5):1547-1553 (1992); Hollinger et al., Proc. Natl. Acad. Sci. USA 90:6444-6448 (1993); Gruber et al., J. Immunol. 152:5368 (1994); and Tuft et al., J. Immunol. 147:60 (1991). Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. A strategy for making bispecific antibody fragments by the use of single-chain Fv (scFv) dimers has also been reported. See Gruber et al., J. Immunol., 152:5368 (1994). Alternatively, the antibodies can be "linear antibodies" as described in Zapata et al. Protein Eng. 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

To produce the chimeric antibodies, the portions derived from two different species (e.g., human constant region and murine variable or binding region) can be joined together chemically by conventional techniques or can be prepared as single contiguous proteins using genetic engineering techniques. The DNA molecules encoding the proteins of both the light chain and heavy chain portions of the chimeric antibody can be expressed as contiguous proteins. The method of making chimeric antibodies is disclosed in U.S. Pat. No. 5,677,427; U.S. Pat. No. 6,120,767; and U.S. Pat. No. 6,329,508, each of which is incorporated by reference in its entirety.

Fully human antibodies may be produced by a variety of techniques. One example is trioma methodology. The basic approach and an exemplary cell fusion partner, SPAZ-4, for use in this approach have been described by Oestberg et al., Hybridoma 2:361-367 (1983); Oestberg, U.S. Pat. No. 4,634,664; and Engleman et al., U.S. Pat. No. 4,634,666 (each of which is incorporated by reference in its entirety).

Human antibodies can also be produced from non-human transgenic animals having transgenes encoding at least a segment of the human immunoglobulin locus. The production and properties of animals having these properties are described in detail by, see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety.

Various recombinant antibody library technologies may also be utilized to produce fully human antibodies. For example, one approach is to screen a DNA library from human B cells according to the general protocol outlined by Huse et al., Science 246:1275-1281 (1989). The protocol described by Huse is rendered more efficient in combination with phage-display technology. See, e.g., Dower et al., WO 91/17271 and McCafferty et al., WO 92/01047; U.S. Pat. No. 5,969,108, (each of which is incorporated by reference in its entirety).

Eukaryotic ribosome can also be used as means to display a library of antibodies and isolate the binding human antibodies by screening against the target antigen, as described in Coia G, et al., J. Immunol. Methods 1: 254 (1-2):191-7 (2001); Hanes J. et al., Nat. Biotechnol. 18(12):1287-92 (2000); Proc. Natl. Acad. Sci. U.S.A. 95(24):14130-5 (1998); Proc. Natl. Acad. Sci. U.S.A. 94(10):4937-42 (1997), each which is incorporated by reference in its entirety.

The yeast system is also suitable for screening mammalian cell-surface or secreted proteins, such as antibodies. Antibody libraries may be displayed on the surface of yeast cells for the purpose of obtaining the human antibodies against a target antigen. This approach is described by Yeung, et al., Biotechnol. Prog. 18(2):212-20 (2002); Boeder, E. T., et al., Nat. Biotechnol. 15(6):553-7 (1997), each of which is herein incorporated by reference in its entirety. Alternatively, human antibody libraries may be expressed intracellularly and screened via the yeast two-hybrid system (WO0200729A2, which is incorporated by reference in its entirety).

Recombinant DNA techniques can be used to produce the recombinant methylation or acetylation site-specific antibodies described herein, as well as the chimeric or humanized methylation or acetylation site-specific antibodies, or any other genetically-altered antibodies and the fragments or conjugate thereof in any expression systems including both prokaryotic and eukaryotic expression systems, such as bacteria, yeast, insect cells, plant cells, mammalian cells (for example, NSO cells).

Once produced, the whole antibodies, their dimers, individual light and heavy chains, or other immunoglobulin forms of the present application can be purified according to standard procedures of the art, including ammonium sulfate precipitation, affinity columns, column chromatography, gel electrophoresis and the like (see, generally, Scopes, R., Protein Purification (Springer-Verlag, N.Y., 1982)). Once purified, partially or to homogeneity as desired, the polypeptides may then be used therapeutically (including extracorporeally) or in developing and performing assay procedures, immunofluorescent staining, and the like. (See, generally, Immunological Methods, Vols. I and II (Lefkovits and Pernis, eds., Academic Press, NY, 1979 and 1981).

Therapeutic Uses

In a further aspect, the disclosure features methods and compositions for therapeutic uses of the peptides or proteins comprising a methylation or acetylation site of the disclosure, and methylation or acetylation site-specific antibodies of the disclosure.

In one embodiment, the disclosure features for a method of treating or preventing cancer in a subject, wherein the cancer is associated with the methylation or acetylation state of a methylation in Table 1 or acetylation site in Table 2, whether methylated or demethylated, comprising: administering to a subject in need thereof a therapeutically effective amount of a peptide comprising a methylation or acetylation site (Table 1 or Table 2) and/or an antibody or antigen-binding fragment thereof that specifically bind a methylation or acetylation site of the disclosure (Table 1 or Table 2). The antibodies maybe full-length antibodies, genetically engineered antibodies, antibody fragments, and antibody conjugates of the disclosure.

The term "subject" refers to a vertebrate, such as for example, a mammal, or a human. Although present application are primarily concerned with the treatment of human subjects, the disclosed methods may also be used for the treatment of other mammalian subjects such as dogs and cats for veterinary purposes.

In one aspect, the disclosure features a method of treating cancer in which a peptide or an antibody that reduces at least one biological activity of a targeted signaling protein is administered to a subject. For example, the peptide or the antibody administered may disrupt or modulate the interaction of the target signaling protein with its ligand. Alternatively, the peptide or the antibody may interfere with, thereby reducing, the down-stream signal transduction of the parent signaling protein. An antibody that specifically binds the arginine or lysine methylation or acetylation site only when the arginine or lysine is methylated or acetylated, and that does not substantially bind to the same sequence when the arginine or lysine is not methylated or acetylated, thereby prevents downstream signal transduction triggered by an methyl-arginine or lysine or acetyl-lysine. Alternatively, an antibody that specifically binds the unmethylated target methylation or acetylation site reduces the methylation or acetylation at that site and thus reduces activation of the protein mediated by methylation or acetylation of that site. Similarly, an unmethylated or unacetylated peptide may compete with an endogenous methylation or acetylation site for same kinases, thereby preventing or reducing the methylation of the endogenous target protein. Alternatively, a peptide comprising a methylated arginine or lysine site of the disclosure but lacking the ability to trigger signal transduction may competitively inhibit interaction of the endogenous protein with the same down-stream ligand(s).

The antibodies of the disclosure may also be used to target cancer cells for effector-mediated cell death. The antibody disclosed herein may be administered as a fusion molecule that includes a methylation or acetylation site-targeting portion joined to a cytotoxic moiety to directly kill cancer cells. Alternatively, the antibody may directly kill the cancer cells through complement-mediated or antibody-dependent cellular cytotoxicity.

Accordingly in one embodiment, the antibodies of the present disclosure may be used to deliver a variety of cytotoxic compounds. Any cytotoxic compound can be fused to the present antibodies. The fusion can be achieved chemically or genetically (e.g., via expression as a single, fused molecule). The cytotoxic compound can be a biological, such as a polypeptide, or a small molecule. As those skilled in the art will appreciate, for small molecules, chemical fusion is used, while for biological compounds, either chemical or genetic fusion can be used.

Non-limiting examples of cytotoxic compounds include therapeutic drugs, radiotherapeutic agents, ribosome-inactivating proteins (RIPs), chemotherapeutic agents, toxic small molecules, toxic peptides, toxic proteins, and mixtures thereof. The cytotoxic drugs can be intracellularly acting cytotoxic drugs, such as short-range radiation emitters, including, for example, short-range, high-energy α-emitters. Enzymatically active toxins and fragments thereof, including ribosome-inactivating proteins, are exemplified by saporin, luffin, momordins, ricin, trichosanthin, gelonin, abrin, etc. Procedures for preparing enzymatically active polypeptides of the immunotoxins are described in WO84/03508 and WO85/03508, which are hereby incorporated by reference. Certain cytotoxic moieties are derived from adriamycin, chlorambucil, daunomycin, methotrexate, neocarzinostatin, and platinum, for example.

Exemplary chemotherapeutic agents that may be attached to an antibody or antigen-binding fragment thereof include taxol, doxorubicin, verapamil, podophyllotoxin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, transplatinum, 5-fluorouracil, vincristin, vinblastin, or methotrexate.

Procedures for conjugating the antibodies with the cytotoxic agents have been previously described and are within the purview of one skilled in the art.

Alternatively, the antibody can be coupled to high energy radiation emitters, for example, a radioisotope, such as $^{131}$I, a γ-emitter, which, when localized at the tumor site, results in a killing of several cell diameters. See, e.g., S. E. Order, "Analysis, Results, and Future Prospective of the Therapeutic Use of Radiolabeled Antibody in Cancer Therapy", Monoclonal Antibodies for Cancer Detection and Therapy, Baldwin et al. (eds.), pp. 303-316 (Academic Press 1985), which is hereby incorporated by reference. Other suitable radioisotopes include α-emitters, such as $^{212}$Bi, $^{213}$Bi, and $^{211}$At, and β-emitters, such as $^{186}$Re and $^{90}$Y.

Because many of the signaling proteins in which arginine or lysine methylation or acetylation sites of the disclosure occur also are expressed in normal cells and tissues, it may also be advantageous to administer a methylation or acetylation site-specific antibody with a constant region modified to reduce or eliminate ADCC or CDC to limit damage to normal cells. For example, effector function of antibodies may be reduced or eliminated by utilizing an IgG1 constant domain instead of an IgG2/4 fusion domain. Other ways of eliminating effector function can be envisioned such as, e.g., mutation of the sites known to interact with FcR or insertion of a peptide in the hinge region, thereby eliminating critical sites required for FcR interaction. Variant antibodies with reduced or no effector function also include variants as described previously herein.

The peptides and antibodies of the disclosure may be used in combination with other therapies or with other agents. Other agents include but are not limited to polypeptides, small molecules, chemicals, metals, organometallic compounds, inorganic compounds, nucleic acid molecules, oligonucleotides, aptamers, spiegelmers, antisense nucleic acids, locked nucleic acid (LNA) inhibitors, peptide nucleic acid (PNA) inhibitors, immunomodulatory agents, antigen-binding fragments, prodrugs, and peptidomimetic compounds. In certain embodiments, the antibodies and peptides of the disclosure may be used in combination with cancer therapies known to one of skill in the art.

In certain aspects, the present disclosure relates to combination treatments comprising a methylation or acetylation site-specific antibody described herein and immunomodulatory compounds, vaccines or chemotherapy. Illustrative examples of suitable immunomodulatory agents that may be used in such combination therapies include agents that block negative regulation of T cells or antigen presenting cells (e.g., anti-CTLA4 antibodies, anti-PD-L1 antibodies, anti-PDL-2 antibodies, anti-PD-1 antibodies and the like) or agents that enhance positive co-stimulation of T cells (e.g., anti-CD40 antibodies or anti 4-1BB antibodies) or agents that increase NK cell number or T-cell activity (e.g., inhibitors such as IMiDs, thalidomide, or thalidomide analogs). Furthermore, immunomodulatory therapy could include cancer vaccines such as dendritic cells loaded with tumor cells, proteins, peptides, RNA, or DNA derived from such cells, patient derived heat-shock proteins (hsp's) or general adjuvants stimulating the immune system at various levels such as CpG, Luivac®, Biostim®, Ribomunyl®, Imudon®, Bronchovaxom® or any other compound or other adjuvant activating receptors of the innate immune system (e.g., toll like receptor agonist, anti-CTLA-4 antibodies, etc.). Also, immunomodulatory therapy could include treatment with cytokines such as IL-2, GM-CSF and IFN-gamma.

Furthermore, combination of antibody therapy with chemotherapeutics could be particularly useful to reduce overall tumor burden, to limit angiogenesis, to enhance tumor accessibility, to enhance susceptibility to ADCC, to result in increased immune function by providing more tumor antigen, or to increase the expression of the T cell attractant LIGHT.

Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, camptothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic anti-tumor compounds may be categorized by their mechanism of action into groups, including, for example, the following classes of agents: anti-metabolites/anti-cancer agents, such as pyrimidine analogs (5-fluorouracil, floxuridine, capecitabine, gemcitabine and cytarabine) and purine analogs, folate inhibitors and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristine, vinblastine, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, mechlorethamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); immuno-modulatory agents (thalidomide and analogs thereof such as lenalidomide (Revlimid, CC-5013) and CC-4047 (Actimid)), cyclophosphamide; anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylprednisolone, prednisone, and prenisolone);

growth factor signal transduction kinase inhibitors; mitochondrial dysfunction inducers and caspase activators; and chromatin disruptors.

In certain embodiments, pharmaceutical compounds that may be used for combinatory anti-angiogenesis therapy include: (1) inhibitors of release of "angiogenic molecules," such as bFGF (basic fibroblast growth factor); (2) neutralizers of angiogenic molecules, such as anti-βbFGF antibodies; and (3) inhibitors of endothelial cell response to angiogenic stimuli, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin $D_3$ analogs, alpha-interferon, and the like. For additional proposed inhibitors of angiogenesis, see Blood et al., Biochim. Biophys. Acta, 1032:89-118 (1990), Moses et al., Science, 248:1408-1410 (1990), Ingber et al., Lab. Invest., 59:44-51 (1988), and U.S. Pat. Nos. 5,092,885, 5,112,946, 5,192,744, 5,202,352, and 6,573,256. In addition, there are a wide variety of compounds that can be used to inhibit angiogenesis, for example, peptides or agents that block the VEGF-mediated angiogenesis pathway, endostatin protein or derivatives, arginine or lysine binding fragments of angiostatin, melanin or melanin-promoting compounds, plasminogen fragments (e.g., Kringles 1-3 of plasminogen), troponin subunits, inhibitors of vitronectin $\alpha_v\beta_3$, peptides derived from Saposin B, antibiotics or analogs (e.g., tetracycline or neomycin), dienogest-containing compositions, compounds comprising a MetAP-2 inhibitory core coupled to a peptide, the compound EM-138, chalcone and its analogs, and naaladase inhibitors. See, for example, U.S. Pat. Nos. 6,395,718, 6,462,075, 6,465,431, 6,475,784, 6,482,802, 6,482,810, 6,500,431, 6,500,924, 6,518,298, 6,521,439, 6,525,019, 6,538,103, 6,544,758, 6,544,947, 6,548,477, 6,559,126, and 6,569,845.

Diagnostic Uses

In a further aspect, the disclosure features methods for detecting and quantitating methylation or acetylation at an arginine or lysine methylation or acetylation site of the disclosure. For example, peptides, including AQUA peptides of the disclosure, and antibodies of the disclosure are useful in diagnostic and prognostic evaluation of cancer, wherein the particular cancer is associated with the methylation or acetylation state of a methylation in Table 1 or acetylation site in Table 2, whether methylated or demethylated.

Methods of diagnosis can be performed in vitro using a biological sample (e.g., blood sample, lymph node biopsy or tissue) from a subject, or in vivo. The methylation state or level at the arginine or lysine residue identified in the corresponding row in Column E of Table 1 or acetylation state or level at the arginine or lysine residue identified in the corresponding row in Column E of Table 2 may be assessed. A change in the methylation or acetylation state or level at the methylation or acetylation site, as compared to a control, indicates that the subject is suffering from, or susceptible to a form of cancer; for example, carcinoma.

In one embodiment, the methylation state or level at a methylation or acetylation site is determined by an AQUA peptide comprising the methylation or acetylation site. The AQUA peptide may be methylated or acetylated or unmethylated or unacetylated at the specified arginine or lysine position.

In another embodiment, the methylation or acetylation state or level at a methylation or acetylation site is determined by an antibody or antigen-binding fragment thereof, wherein the antibody specifically binds the methylation or acetylation site. The antibody may be one that only binds to the methylation or acetylation site when the arginine or lysine residue is methylated or acetylated, but does not bind to the same sequence when the arginine or lysine is not methylated or acetylated; or vice versa.

In particular embodiments, the antibodies of the present application are attached to labeling moieties, such as a detectable marker. One or more detectable labels can be attached to the antibodies. Exemplary labeling moieties include radiopaque dyes, radiocontrast agents, fluorescent molecules, spin-labeled molecules, enzymes, or other labeling moieties of diagnostic value, particularly in radiologic or magnetic resonance imaging techniques.

A radiolabeled antibody in accordance with this disclosure can be used for in vitro diagnostic tests. The specific activity of an antibody, binding portion thereof, probe, or ligand, depends upon the half-life, the isotopic purity of the radioactive label, and how the label is incorporated into the biological agent. In immunoassay tests, the higher the specific activity, in general, the better the sensitivity. Radioisotopes useful as labels, e.g., for use in diagnostics, include iodine ($^{131}$I or $^{125}$I), indium ($^{111}$I), technetium ($^{99}$Tc), phosphorus ($^{32}$P), carbon ($^{14}$C), and tritium ($^3$H), or one of the therapeutic isotopes listed above.

Fluorophore and chromophore labeled biological agents can be prepared from standard moieties known in the art. Since antibodies and other proteins absorb light having wavelengths up to about 310 nm, the fluorescent moieties may be selected to have substantial absorption at wavelengths above 310 nm, such as for example, above 400 nm. A variety of suitable fluorescers and chromophores are described by Stryer, Science, 162:526 (1968) and Brand et al., Annual Review of Biochemistry, 41:843-868 (1972), which are hereby incorporated by reference. The antibodies can be labeled with fluorescent chromophore groups by conventional procedures such as those disclosed in U.S. Pat. Nos. 3,940,475, 4,289,747, and 4,376,110, which are hereby incorporated by reference.

The control may be parallel samples providing a basis for comparison, for example, biological samples drawn from a healthy subject, or biological samples drawn from healthy tissues of the same subject. Alternatively, the control may be a pre-determined reference or threshold amount. If the subject is being treated with a therapeutic agent, and the progress of the treatment is monitored by detecting the arginine or lysine methylation or acetylation state level at a methylation or acetylation site of the disclosure, a control may be derived from biological samples drawn from the subject prior to, or during the course of the treatment.

In certain embodiments, antibody conjugates for diagnostic use in the present application are intended for use in vitro, where the antibody is linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. In certain embodiments, secondary binding ligands are biotin and avidin or streptavidin compounds.

Antibodies of the disclosure may also be optimized for use in a flow cytometry (FC) assay to determine the activation/methylation status of a target signaling protein in subjects before, during, and after treatment with a therapeutic agent targeted at inhibiting arginine or lysine methylation or acetylation at the methylation or acetylation site disclosed herein. For example, bone marrow cells or peripheral blood cells from patients may be analyzed by flow cytometry for target signaling protein methylation or acetylation, as well as for markers identifying various hematopoietic cell types. In this manner, activation status of the malignant cells may be specifically characterized. Flow cytometry may be carried out according to standard methods. See, e.g., Chow et al., *Cytometry (Communications in Clinical Cytometry)* 46: 72-78 (2001).

Alternatively, antibodies of the disclosure may be used in immunohistochemical (IHC) staining to detect differences in signal transduction or protein activity using normal and diseased tissues. IHC may be carried out according to well-known techniques. See, e.g., Antibodies: A Laboratory Manual, supra.

Peptides and antibodies of the disclosure may be also be optimized for use in other clinically-suitable applications, for example bead-based multiplex-type assays, such as IGEN, Luminex™ and/or Bioplex™ assay formats, or otherwise optimized for antibody arrays formats, such as reversed-phase array applications (see, e.g. Paweletz et al., *Oncogene* 20(16): 1981-89 (2001)). Accordingly, in another embodiment, the disclosure features a method for the multiplex detection of the methylation or acetylation state or level at two or more methylation or acetylation sites of the disclosure (Table 1 or Table 2) in a biological sample, the method comprising utilizing two or more antibodies or AQUA peptides of the disclosure. In one embodiment, two to five antibodies or AQUA peptides of the disclosure are used. In another embodiment, six to ten antibodies or AQUA peptides of the disclosure are used, while in another embodiment eleven to twenty antibodies or AQUA peptides of the disclosure are used.

In certain embodiments the diagnostic methods of the application may be used in combination with other cancer diagnostic tests.

The biological sample analyzed may be any sample that is suspected of having abnormal arginine or lysine methylation or acetylation at a methylation or acetylation site of the disclosure, such as a homogenized neoplastic tissue sample.

Screening Assays

In another aspect, the disclosure features a method for identifying an agent that modulates arginine or lysine methylation at a methylation or acetylation site of the disclosure, comprising: a) contacting a candidate agent with a peptide or protein comprising a methylation or acetylation site of the disclosure; and b) determining the methylation state or level at the methylation or acetylation site. A change in the methylation or acetylation level of the specified arginine or lysine in the presence of the test agent, as compared to a control, indicates that the candidate agent potentially modulates arginine or lysine methylation at a methylation or acetylation site of the disclosure.

In one embodiment, the acetylation level of K155 of C3 is determined to be elevated in the sera of NSCLC patients. In one aspect, the methylation level of R1593 of ARID1A is determined to be significantly lower in the sera of NSCLC than other types of cancer (eg., acute myeloid leukemia, breast cancer). In another aspect, the acetylation of K298 of albumin is determined to be elevated in in NSCLC.

In one embodiment, the methylation or acetylation state or level at a methylation or acetylation site is determined by an AQUA peptide comprising the methylation or acetylation site. The AQUA peptide may be methylated or acetylated or unmethylated or unacetylated at the specified arginine or lysine position.

In another embodiment, the methylation or acetylation state or level at a methylation or acetylation site is determined by an antibody or antigen-binding fragment thereof, wherein the antibody specifically binds the methylation or acetylation site. The antibody may be one that only binds to the methylation or acetylation site when the arginine or lysine residue is methylated or acetylated, but does not bind to the same sequence when the arginine or lysine is not methylated or not acetylated; or vice versa.

In particular embodiments, the antibodies of the present application are attached to labeling moieties, such as a detectable marker.

The control may be parallel samples providing a basis for comparison, for example, the methylation level of the target protein or peptide in absence of the testing agent. Alternatively, the control may be a pre-determined reference or threshold amount.

Immunoassays

In another aspect, the present application concerns immunoassays for binding, purifying, quantifying and otherwise generally detecting the methylation or acetylation state or level at a methylation or acetylation site of the disclosure.

Assays may be homogeneous assays or heterogeneous assays. In a homogeneous assay the immunological reaction usually involves a methylation or acetylation site-specific antibody of the disclosure, a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels that may be used include free radicals, radioisotopes, fluorescent dyes, enzymes, bacteriophages, coenzymes, and so forth.

In a heterogeneous assay approach, the reagents are usually the specimen, a methylation or acetylation site-specific antibody of the disclosure, and suitable means for producing a detectable signal. Similar specimens as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal using means for producing such signal. The signal is related to the presence of the analyte in the specimen. Means for producing a detectable signal include the use of radioactive labels, fluorescent labels, enzyme labels, and so forth.

Methylation or acetylation site-specific antibodies disclosed herein may be conjugated to a solid support suitable for a diagnostic assay (e.g., beads, plates, slides or wells formed from materials such as latex or polystyrene) in accordance with known techniques, such as precipitation.

In certain embodiments, immunoassays are the various types of enzyme linked immunoadsorbent assays (ELISAs) and radioimmunoassays (RIA) known in the art. Immunohistochemical detection using tissue sections is also particularly useful. However, it will be readily appreciated that detection is not limited to such techniques, and Western blotting, dot and slot blotting, FACS analyses, and the like may also be used. The steps of various useful immunoassays have been described in the scientific literature, such as, e.g., Nakamura et al., in Enzyme Immunoassays: Heterogeneous and Homogeneous Systems, Chapter 27 (1987), incorporated herein by reference.

In general, the detection of immunocomplex formation is well known in the art and may be achieved through the application of numerous approaches. These methods are based upon the detection of radioactive, fluorescent, biological or enzymatic tags. Of course, one may find additional advantages through the use of a secondary binding ligand such as a second antibody or a biotin/avidin ligand binding arrangement, as is known in the art.

The antibody used in the detection may itself be conjugated to a detectable label, wherein one would then simply detect this label. The amount of the primary immune complexes in the composition would, thereby, be determined.

Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are washed extensively to remove any non-specifically bound labeled secondary antibodies or ligands, and the remaining label in the secondary immune complex is detected.

An enzyme linked immunoadsorbent assay (ELISA) is a type of binding assay. In one type of ELISA, methylation or acetylation site-specific antibodies disclosed herein are immobilized onto a selected surface exhibiting protein affinity, such as a well in a polystyrene microtiter plate. Then, a suspected neoplastic tissue sample is added to the wells. After binding and washing to remove non-specifically bound immune complexes, the bound target signaling protein may be detected.

In another type of ELISA, the neoplastic tissue samples are immobilized onto the well surface and then contacted with the methylation or acetylation site-specific antibodies disclosed herein. After binding and washing to remove non-specifically bound immune complexes, the bound methylation or acetylation site-specific antibodies are detected.

Irrespective of the format used, ELISAs have certain features in common, such as coating, incubating or binding, washing to remove non-specifically bound species, and detecting the bound immune complexes.

The radioimmunoassay (RIA) is an analytical technique which depends on the competition (affinity) of an antigen for antigen-binding sites on antibody molecules. Standard curves are constructed from data gathered from a series of samples each containing the same known concentration of labeled antigen, and various, but known, concentrations of unlabeled antigen. Antigens are labeled with a radioactive isotope tracer. The mixture is incubated in contact with an antibody. Then the free antigen is separated from the antibody and the antigen bound thereto. Then, by use of a suitable detector, such as a gamma or beta radiation detector, the percent of either the bound or free labeled antigen or both is determined. This procedure is repeated for a number of samples containing various known concentrations of unlabeled antigens and the results are plotted as a standard graph. The percent of bound tracer antigens is plotted as a function of the antigen concentration. Typically, as the total antigen concentration increases the relative amount of the tracer antigen bound to the antibody decreases. After the standard graph is prepared, it is thereafter used to determine the concentration of antigen in samples undergoing analysis.

In an analysis, the sample in which the concentration of antigen is to be determined is mixed with a known amount of tracer antigen. Tracer antigen is the same antigen known to be in the sample but which has been labeled with a suitable radioactive isotope. The sample with tracer is then incubated in contact with the antibody. Then it can be counted in a suitable detector which counts the free antigen remaining in the sample. The antigen bound to the antibody or immunoadsorbent may also be similarly counted. Then, from the standard curve, the concentration of antigen in the original sample is determined.

Pharmaceutical Formulations and Methods of Administration

Methods of administration of therapeutic agents, particularly peptide and antibody therapeutics, are well-known to those of skill in the art.

Peptides of the disclosure can be administered in the same manner as conventional peptide type pharmaceuticals. In some embodiments, peptides are administered parenterally, for example, intravenously, intramuscularly, intraperitoneally, or subcutaneously. When administered orally, peptides may be proteolytically hydrolyzed. Therefore, oral application may not be usually effective. However, peptides can be administered orally as a formulation wherein peptides are not easily hydrolyzed in a digestive tract, such as liposome-microcapsules. Peptides may be also administered in suppositories, sublingual tablets, or intranasal spray.

If administered parenterally, an exemplary pharmaceutical composition is an aqueous solution that, in addition to a peptide of the disclosure as an active ingredient, may contain for example, buffers such as phosphate, acetate, etc., osmotic pressure-adjusting agents such as sodium chloride, sucrose, and sorbitol, etc., antioxidative or antioxygenic agents, such as ascorbic acid or tocopherol and preservatives, such as antibiotics. The parenterally administered composition also may be a solution readily usable or in a lyophilized form which is dissolved in sterile water before administration.

The pharmaceutical formulations, dosage forms, and uses described below generally apply to antibody-based therapeutic agents, but are also useful and can be modified, where necessary, for making and using therapeutic agents of the disclosure that are not antibodies.

To achieve the desired therapeutic effect, the methylation or acetylation site-specific antibodies or antigen-binding fragments thereof can be administered in a variety of unit dosage forms. The dose will vary according to the particular antibody. For example, different antibodies may have different masses and/or affinities, and thus require different dosage levels. Antibodies prepared as Fab or other fragments will also require differing dosages than the equivalent intact immunoglobulins, as they are of considerably smaller mass than intact immunoglobulins, and thus require lower dosages to reach the same molar levels in the patient's blood. The dose will also vary depending on the manner of administration, the particular symptoms of the patient being treated, the overall health, condition, size, and age of the patient, and the judgment of the prescribing physician. Dosage levels of the antibodies for human subjects are generally between about 1 mg per kg and about 100 mg per kg per patient per treatment, such as for example, between about 5 mg per kg and about 50 mg per kg per patient per treatment. In terms of plasma concentrations, the antibody concentrations may be in the range from about 25 µg/mL to about 500 µg/mL. However, greater amounts may be required for extreme cases and smaller amounts may be sufficient for milder cases.

Administration of an antibody will generally be performed by a parenteral route, typically via injection such as intra-articular or intravascular injection (e.g., intravenous infusion) or intramuscular injection. Other routes of administration, e.g., oral (p.o.), may be used if desired and practicable for the particular antibody to be administered. An antibody can also be administered in a variety of unit dosage forms and their dosages will also vary with the size, potency, and in vivo half-life of the particular antibody being administered. Doses of a methylation or acetylation site-specific antibody will also vary depending on the manner of administration, the particular symptoms of the patient being treated, the overall health, condition, size, and age of the patient, and the judgment of the prescribing physician.

The frequency of administration may also be adjusted according to various parameters. These include the clinical response, the plasma half-life of the antibody, and the levels of the antibody in a body fluid, such as, blood, plasma, serum, or synovial fluid. To guide adjustment of the frequency of administration, levels of the antibody in the body fluid may be monitored during the course of treatment.

Formulations particularly useful for antibody-based therapeutic agents are also described in U.S. Patent App. Publication Nos. 20030202972, 20040091490 and 20050158316. In certain embodiments, the liquid formulations of the application are substantially free of surfactant and/or inorganic salts. In another specific embodiment, the liquid formulations have a pH ranging from about 5.0 to about 7.0. In yet another specific embodiment, the liquid formulations comprise histidine at a concentration ranging from about 1 mM to about 100 mM. In still another specific embodiment, the liquid formulations comprise histidine at a concentration ranging from 1 mM to 100 mM. It is also contemplated that the liquid formulations may further comprise one or more excipients such as a saccharide, an amino acid (e.g., arginine, lysine, and methionine) and a polyol. Additional descriptions and methods of preparing and analyzing liquid formulations can be found, for example, in PCT publications WO 03/106644, WO 04/066957, and WO 04/091658.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the pharmaceutical compositions of the application.

In certain embodiments, formulations of the subject antibodies are pyrogen-free formulations which are substantially free of endotoxins and/or related pyrogenic substances. Endotoxins include toxins that are confined inside microorganisms and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1): 223 (2000)). When therapeutic proteins are administered in amounts of several hundred or thousand milligrams per kilogram body weight, as can be the case with monoclonal antibodies, it is advantageous to remove even trace amounts of endotoxin.

The amount of the formulation which will be therapeutically effective can be determined by standard clinical techniques. In addition, in vitro assays may optionally be used to help identify optimal dosage ranges. The precise dose to be used in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. The dosage of the compositions to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. For example, the actual patient body weight may be used to calculate the dose of the formulations in milliliters (mL) to be administered. There may be no downward adjustment to "ideal" weight. In such a situation, an appropriate dose may be calculated by the following formula:

Dose (mL)=[patient weight (kg)×dose level (mg/kg)/drug concentration (mg/mL)]

For the purpose of treatment of disease, the appropriate dosage of the compounds (for example, antibodies) will depend on the severity and course of disease, the patient's clinical history and response, the toxicity of the antibodies, and the discretion of the attending physician. The initial candidate dosage may be administered to a patient. The proper dosage and treatment regimen can be established by monitoring the progress of therapy using conventional techniques known to those of skill in the art.

The formulations of the application can be distributed as articles of manufacture comprising packaging material and a pharmaceutical agent which comprises, e.g., the antibody and a pharmaceutically acceptable carrier as appropriate to the mode of administration. The packaging material will include a label which indicates that the formulation is for use in the treatment of prostate cancer.

Kits

Antibodies and peptides (including AQUA peptides) of the disclosure may also be used within a kit for detecting the methylation or acetylation state or level at a methylation or acetylation site of the disclosure, comprising at least one of the following: an AQUA peptide comprising the methylation or acetylation site, or an antibody or an antigen-binding fragment thereof that binds to an amino acid sequence comprising the methylation or acetylation site. Such a kit may further comprise a packaged combination of reagents in predetermined amounts with instructions for performing the diagnostic assay. Where the antibody is labeled with an enzyme, the kit will include substrates and co-factors required by the enzyme. In addition, other additives may be included such as stabilizers, buffers and the like. The relative amounts of the various reagents may be varied widely to provide for concentrations in solution of the reagents that substantially optimize the sensitivity of the assay. Particularly, the reagents may be provided as dry powders, usually lyophilized, including excipients that, on dissolution, will provide a reagent solution having the appropriate concentration.

The following Examples are provided only to further illustrate the disclosure, and are not intended to limit its scope, except as provided in the claims appended hereto. The disclosure encompasses modifications and variations of the methods taught herein which would be obvious to one of ordinary skill in the art.

EXAMPLES

Example 1

Identification of Methylation Sites in HCT116 Cells

Protein methylation site identification using methyl-motif antibodies to enrich methylated peptides and analysis of the enriched peptides by LC-MS/MS was developed Tryptic peptides from approximately 10 mg of protein extract derived from either cell lines or tissue samples, and 100-250 µg of methylation specific antibodies.

From a single experiment using Me-R4-100 (Cell Signaling Technology, #8015) antibody to immunoprecipitate tryptic peptides from HCT116 cells, 1106 MMA sites from 1743 unique methylated peptides from 570 proteins were identified. The R*GG (D5A12) (CST #8711) antibody identified 942 MMA sites from 1456 unique monomethyl arginine peptides from 489 proteins. With a ADMA-specific monoclonal antibody (D4H5), 226 ADMA sites from 287 unique peptides from 97 proteins were identified. Using a different ADMA-specific monoclonal antibody (D6A8) with HCT116 tryptic peptides, 335 ADMA sites were identified from 440 peptides from 140 proteins. HCT116 tryptic peptides were used in lysine methylation profiling experiments with polyclonal anti-methyl lysine antibodies against monomethyl-lysine (Kme1), dimethyl-lysine (Kme2), and trimethyl-lysine (Kme3). Kme1 antibody identified 132 mono methyl lysine sites from 111 proteins; Kme2 and Kme3 identified 35 and 31 sites, respectively, from about 20 proteins were identified.

Example 2

Protein Lysine Methylation Sites Identified in HCT116 Cells

Using Kme1, Kme2, and Kme3 antibodies in HCT116 cells, in total 165 lysine methylation sites were identified: 132 monomethyl K, 35 dimethyl K, and 31 trimethyl K. There were far fewer lysine methylation sites than arginine methylation sites. Western blot analysis with lysine methylation antibodies showed fewer bands than arginine methylation blots, which reflect that there are fewer lysine methylation sites in the cells. To rule out the possibility that fewer lysine methylation site identifications was due to antibody affinity/specificity issues, a diverse population of dimethylated peptides were generated by reductive amination reaction (Hsu, J. L., et. al., (2003) Stable-isotope dimethyl labeling for quantitative proteomics. *Analytical Chemistry* 75, 6843-6852), and a mix of dimethyl peptides and unlabeled peptides from HCT116 cells at a ratio of 1:9 (1 mg labeled: 9 mg unlabeled) were used to do immunoaffinity enrichment using dimethyl lysine antibody. From this experiment, 3857 dimethylated lysine peptides corresponding to 2763 unique sites were identified. The fact that the antibody selectively enriched a diverse population of dimethylated sequences suggests that the small set of peptides identified in vivo from the HCT116 cells is not due to antibody affinity/specificity.

In the lysine methylation site profiling experiments using tryptic peptides from HCT116 cells, several lysine methylation sites were identified, including components of the transcription complex such as transcription factors POLR2B, POLR3B. Also identified were lysine methylation on several lysine methyl transferases including dimethylation of EZH2, mono-, di-, and tri-methylation of SETDB1, and mono-methylation of EZH1 (Table 1).

Example 3

Profiling Arginine Methylation of Mouse Brain and Mouse Embryo

Protein arginine methylation in mouse brain (from 3 month old mice) and mouse embryo (E16-17) were profiled by immunoaffinity enrichment using various arginine methylation antibodies and LC-MS/MS analysis. In total, 807 MMA sites on 453 proteins from mouse brain and 598 MMA sites on 331 proteins from mouse embryo using a combination of D5A12 and Me-R4-1000 antibodies we identified, corresponding to a total of 1070 unique MMA sites from two tissues. Asymmetric dimethylated peptides were enriched with D4H5 and D6A8 antibodies or the combination of the two, and 697 ADMA sites on 321 proteins were identified. MS/MS spectra of many proteins known to be brain-specific were identified in the brain samples but not in embryo as expected.

To demonstrate a quantitative assessment of the IAP-LC-MS/MS method for identifying and quantifying methyl proteins among samples, the technical variation of immunoprecipitation using monomethyl arginine antibodies were evaluated in three independent IAPB. The experiments were performed using the same batch of mouse embryo peptides with mixture of the two MMA antibodies Me-R4-100 and D5A12. Each sample was processed separately and the resulting enriched methylated peptides were analyzed by LC-MS/MS in duplicate runs. In total, 818 unique arginine monomethylation peptides were identified, among which, over 66% of the sites were identified in common from three IAPB. Each site was quantified by label-free techniques using Skyline software. The median variation (% CV, percent coefficient of variation) between replicate injections of matched methylated peptides for the three independent IAP samples were of 14%, 13% and 9% respectively. The variation associated with the IAP method was illustrated from the median % CV across three independent IAPB for the mouse embryo samples, and was determined to be 13. In addition, 80% of the methylation sites that were quantified had % CVs lower than 20%. The results from this experiment demonstrates that the IAP-LC-MS/MS method is quantitatively reproducible when experiments are performed in parallel, and the LC-MS/MS analysis is collected in the same period of time.

To have a better understanding of the abundance of arginine-methylated proteins in different tissues, the data from the MMA profiling of mouse brain and mouse embryo in biological were analyzed in triplicate experiments using Skyline software to compare the relative abundance of common methylation sites between the two tissues. In these experiments, a total of 10 mg of peptides from either mouse brain or mouse embryo were used in each IAP experiment using the same amount of MMA antibodies, the IAPB were done in parallel at the same time, each IAP sample was analyzed in duplicate LC-MS/MS runs. In total, there were 6 datasets from mouse brain and 6 datasets from mouse embryo. MS1 precursor intensities of methylated peptides were compared between corresponding MS runs from mouse brain versus mouse embryo and averaged for each tissues to obtain the relative abundance of common methylation sites, which provided confident quantitative results of over 1000 unique arginine monomethylation sites from the tissues. An arbitrary fold change threshold of 5 was set as a quantitative cut-off to indicate whether a particular methylation peptide was more abundant in one tissue than the other. From this analysis, there were in total 480 and 272 unique monomethylation peptides with high abundance in mouse brain and embryo respectively, including 31 and 12 monomethylation peptides that existed in brain and embryo only, respectively. A scatter plot of log 2 intensity ratio of Brain/Embryo of each methylation site vs. total peptide intensity was made to represent the peptides that are specific or rich in one particular mouse tissue. For statistic analysis, the p-value was provided for each ratio by t-test. Due to the biological variation of mouse brain, many monomethylation peptides that were abundant in brain were associated with high p-value. The IAP experiment results are consistent with western blot analysis of the lysates from the two tissues. The patterns of arginine methylation from the two tissues indicate that arginine methylation does vary in both directions for distinct protein bands.

Protein immunoprecipitation of mouse brain and embryo lysates was performed using a mix of D5A12 and Me-R4-100 MMA antibodies, followed by western blot analysis using protein specific antibodies to confirm the results. PABP1 was more abundant in mouse embryo, and correspondingly methylated PABP1 was also more abundant in mouse embryo. SNIP showed similar abundance in mouse brain and mouse embryo, but was only methylated in mouse brain. This indicates some of the tissue specific methylation observed was due to different protein expression in different tissues, but some other tissue specific methylation is due to the different level of the methylation on the relatively equally expressed proteins. Other types of validation studies such as western blot analysis or total proteome profiling can be performed for important sites that have been identified by IAP-MS experiments.

Additional experimental detail may be found in Guo et al., 2014, Mol. Cell. Proteomics, 13:372-387, which is incorporated herein by reference in its entirety.

Example 4

Identification of Methylation and Acetylation Sites in Human Serum

Serum of Cancer Patients—

Serum samples of 4 patients of AML, BC and NSCLC were purchased from Proteogenex (Culver City, Calif.), respectively.

Tryptic Digestion of Serum—

Equal volume of serum (50 μL for pooled sample and 250 μLL for individual sample) was mixed with urea lysis buffer (9M sequanol grade Urea, 20 mM HEPES pH 8.0, 1 mM b-glycerophosphate, 1 mM sodium vanadate, 2.5 mM sodium pyrophosphate) at the ratio of 1:2 to get the final concentration of urea of 6M. The mixture was centrifuged at 16,000×g for 15 min at 4° C. Supernatants were collected and reduced with 4.5 mM DTT for 30 min at 55° C. Reduced lysates were alkylated with iodoacetimide (0.095 g per 5 mL $H_2O$) for 15 min at room temperature in the dark. Samples were diluted 1:3 with 20 mM HEPES pH 8.0 and digested overnight with 10 ug/mL trypsin-TPCK (Worthington, #LS003740). Digested peptide lysates were acidified with 1% TFA and peptides were desalted over 360 mg SEP PAK Classic C18 columns (Waters, #WAT051910). Peptides were eluted with 40% acetonitrile in 0.1% TFA, dried under vacuum, and stored at −80° C.

Immunoprecipitation—

Enrichment of post-translational modified peptides were done using corresponding PTMScan motif antibodies following the protocols described previously. Briefly, saturating amounts of the indicated antibodies were bound to 25-30 mL packed Protein A agarose beads (Roche) overnight at 4° C. Lyophilized serum peptides were resuspended in MOPS IAP buffer (50 mM MOPS pH 7.2, 10 mM $KH_2PO_4$, 50 mM NaCl) and centrifuged 5 min at 12,000 rpm in a MiniSpin microcentrifuge (Eppendorf). Supernatants were mixed with PTMScan Reagent-Bead slurries 2 hours at 4° C. Beads were pelleted by centrifugation 30 seconds at 5,400 rpm in a MiniSpin microcentrifuge at 4° C. Beads were washed three times with 1.5 mL IAP buffer containing 1% NP-40 and three times with 1 mL water (Burdick and Jackson). Peptides were eluted from beads with 0.15% TFA (sequential elutions of 40 mL followed by 35 mL, 10 min each at room temperature). Eluted peptides were desalted over tips packed with Empore C18 (Sigma) and eluted with 40% acetonitrile in 0.1% TFA. Eluted peptides were dried under vacuum and subject to a second, in-solution trypsin digest using 250 ng of sequencing grade trypsin (Promega) in 50 mM ammonium bicarbonate/5% acetonitrile for 2 hours at 37° C. Samples were acidified with TFA and re-purified over C18 tips as before.

Imac—

IMAC enrichment was performed as previously described. Nickel-agarose beads (Invitrogen) were treated with EDTA to remove the Nickel, washed 3× with $H_2O$, loaded with aqueous $FeCl_3$ for 30 min, and washed. For phosphopeptide enrichment 10 ml $Fe^{3+}$-agarose slurry was added to peptide digested from 10 ml of serum in 1 mL 0.1% TFA/80% acetonitrile for 30 min at room temperature. Unbound peptides were removed by washing 3× with 0.1% TFA/80% MeCN. Bound peptides were eluted with 2×50 mL of 2.5% ammonia/50% acetonitrile solution for 5 min. The pH of the eluent was immediately adjusted to acidic by 20% TFA and dried in a speed-vac. Samples were resuspended in 50 mL 0.15% TFA, desalted over C-18 and dried as previously described.

LC-MS/MS Analysis—

Immunoprecipitated peptides were resuspended in 0.125% formic acid and separated on a reversed-phase $C_{18}$ column (75 mm ID×10 cm) packed into a PicoTip emitter (~8 mm ID) with Magic $C_{18}$ AQ (100 Å×5 mm). Each sample was split and analytical replicate injections were run to increase the number of identifications and provide metrics for analytical reproducibility of the method. For antibody enrichment peptides from ~120 mL serum were run per injection, for IMAC peptides from ~5 mL serum were run per injection. Replicate injections were run non-sequentially to reduce artificial changes in peptide abundance due to changes in instrument performance over time. One replicate of each sample was injected, then the second replicate in reverse order. Peptides were eluted using a 120-minute or 150-minute linear gradient of acetonitrile in 0.125% formic acid delivered at 280 nL/min. Tandem mass spectra were collected in a data-dependent manner with an LTQ-Orbitrap ELITE mass spectrometer running XCalibur 2.0.7 SP1 using a top-twenty MS/MS method, a dynamic repeat count of one, and a repeat duration of 30 sec. Real time recalibration of mass error was performed using lock mass with a singly charged polysiloxane ion m/z=371.101237. The data associated with this manuscript may be downloaded from PRIDE using the following link:

MS/MS spectra were evaluated using SEQUEST and the Core platform from Harvard University. Files were searched against the NCBI *Homo sapiens* FASTA database updated on Jun. 27, 2011 containing 34,899 forward and 34,899 reverse sequences. A mass accuracy of +/−50 ppm was used for precursor ions and 1 Da for product ions. Enzyme specificity was limited to trypsin, with at least one tryptic (K- or R-containing) terminus required per peptide and up to four mis-cleavages allowed. Cysteine carboxamidomethylation was specified as a static modification, oxidation of methionine residues was allowed, and corresponding PTM was allowed for each enrichment sample set. Reverse decoy databases were included for all searches to estimate false discovery rates, and filtered using a 1% FDR in the Linear Discriminant module of Core. Results were further narrowed by mass accuracy based on clustering of forward and reverse assignments in Xcorr versus mass error plots. Typically forward database assignments cluster within −/+5 ppm of calculated m/z, so results were limited to peptides that fall within that range. A larger mass error range (−/+50 ppm) was used for the searches to allow for identification even if the lock mass signal was not adequate for accurate mass calibration. Peptides were also manually filtered using reagent-specific criteria.

All quantitative results were generated using Progenesis V4.1 (Waters Cooperation) and Skyline Version 3.1 to extract the integrated peak area of the corresponding peptide assignments according to previously published protocols. Extracted ion chromatograms for peptide ions that changed in abundance between samples were manually reviewed to ensure accurate quantitation in Skyline. Statistical analysis of the quantitative data was done using two-tail t-test between two cancer groups in Excel. And the max negative log-p value from three comparison pairs was used to indicate whether there existed significant abundance change of a certain PTM site between two cancer groups. Heat map of the quantitative data was generated and clustered in Spotfire DecisionSite (TIBCO Software AB) version 9.1.2.

Western Blotting—

Equal volume of serum samples were mixed with SDS-PAGE sample buffer (Cell Signaling Technology, Inc., #7723,) and run on 4-20% gradient Tris-glycine gels (Invitrogen). For pan-AcK and pan-Rme western blots, serum was diluted 10 fold and 20 µL was loaded. For For albumin, serum was diluted by 10,000 fold and 20 µL was loaded; while for FETUA, serum was diluted 200 fold and 20 µL was loaded. Proteins were transferred to nitrocellulose (Millipore) and blocked for 1 hour in 5% nonfat dry milk (Sigma) in TBS. Motif antibody for pan-AcK (#13420) and pan-Rme (#8015, 8711), primary antibodies for albumin (#4929) were incubated in 5% BSA in TBS plus 0.1% Tween-20 (TBS-T) overnight at 4° C. Membranes were washed 3 times with TBS-T, incubated with anti-rabbit secondary antibody (#5366, Cell Signaling Technology) for 1 hour at room temperature in 5% milk TBS-T, washed 3 times with TBS-T, dried, and developed on the Odyssey near-infrared imaging system (LI-COR). All antibodies were from Cell Signaling Technology, Inc.

Among the PTMs surveyed, lysine acetylation and arginine mono-methylation were identified as the most abundant types of PTM in cancer patients' sera. At 1% FDR, 796 unique AcK sites in the sera of 12 cancer patients were identified (see Table 2), of which, 612 AcK sites were successfully quantified based on the criteria of the chromatographic shapes and the signals of their extracted ion chromatograms of precursor ions; by the same criteria, 808 unique Rme sites were identified (see Table 1), and 621 sites were quantified.

For AcK sites, the top five protein categories are secreted protein, receptor/channel/transporter/cell surface protein, adhesion/extracellular protein, chromatin/DNA-binding/DNA repair/DNA replication protein and transcriptional regulator. Albumin was identified as one of the most heavily acetylated protein with a total number of 76 unique AcK sites. Heavy acetylation was observed on other serum abundant proteins as well including alpha-2-macroglobulin and serotransferrin with a total number of 35 and 29 unique AcK sites identified, respectively. Actually, a decent fraction of the unique AcK sites (190 out of 796) were identified in top 12 abundant serum proteins. For Rme sites, we identified only 4 out of 808 unique Rme sites from top 12 abundant serum proteins. Therefore, the top five protein categories for Rme are receptor/channel/transporter/cell surface protein, RNA processing, transcriptional regulator, adhesion/extracellular protein and adaptor/scaffold. We identified a large number unique Rme sites in various heterogeneous nuclear ribonucleoproteins isoforms, and most of which were identified before. However, the existence of the sites in serum/plasma was not reported by any of the previous studies. There were only 35 proteins identified in common between the results of AcK and Rme enrichment. We also compared our results with a recent large-scale plasma proteome study using iTRAQ labeling and offline fractionation prior to LC-MS/MS analysis, which identified over 5300 proteins with high confidence. There was a medium to small fraction of proteins, 206 out of 569 for AcK, and 205 out of 799 for Rme that were identified in the large-scale study.

The average intensity of acetylation of K155 of C3 showed 8.1 and 4.4 fold increases in NSCLC than AML and BC; while 5.4 and 4.3 fold decreases of arginine methylation level of R1593 of ARID1A were observed in NSCLC comparing to AML and BC. Both sites were represented by peptides with good quality MS/MS spectra. Inconsistent patter of intensity of AcK of patient #4 of NSCLC compared to patients #1, #2 and #3 was exampled by several sites of acetylation of albumin. While the average intensity of acetylation of K298 of albumin in NSCLC patients #1, #2 and #3 showed 9.7 and 2.9 fold increases as compared to those in AML and BC; the site had comparable intensity in patient #4 of NSCLC with those in AML and BC. Although there were intensity changes observed at several AcK sites of albumin, the overall protein level of albumin was not changed. It is worth noting that histological diagnosis of #4 NSCLC patient (with 35 years of smoking history) was squamous cell carcinoma; while the histological diagnosis of #1, #2 and #3 patients (non-smokers) of NSCLC was adenocarcinoma.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09856315B2). An electronic copy of the "Sequence Listing" will also be available from the USPTO upon request and payment of the fee set forth in 37 CFR 1.19(b)(3).

What is claimed is:

1. An isolated antibody or antigen-binding fragment thereof that specifically binds to a polypeptide comprising a lysine residue when said lysine residue is methylated, and does not bind to said polypeptide when said lysine residue is not methylated, wherein said polypeptide comprises an amino acid sequence selected from the group consisting of SEQ ID NOS: 4386, 4400, 4419, 4422, 4423, 4427, 4430, 4431, 4437, 4443, 4457, 4459, 4477, 4479, 4481, 4483, 4489, 4493, and 4506, and wherein said lysine is the lysine at position 7 in each of the amino acid sequences.

2. The antibody according to claim 1, wherein said antibody or antibody fragment is selected from the group consisting of a polyclonal antibody, a monoclonal antibody or antibody fragment, a recombinant antibody, a camelid antibody, a bispecific antibody, a diabody, a chimerized or chimeric antibody or antibody fragment, a humanized antibody or antibody fragment, a deimmunized human antibody or antibody fragment, a fully human antibody or antibody fragment, a single chain antibody, an Fv, an Fd, an Fab, an Fab', and an F(ab')$_2$.

3. The antibody or antigen-binding fragment thereof according to claim 2, wherein the antibody is a polyclonal antibody.

4. The antibody or antigen-binding fragment thereof according to claim 2, wherein the antibody is a monoclonal antibody.

5. The antibody or antigen-binding fragment thereof according to claim 4, wherein the antibody or antibody fragment is conjugated to a cytotoxic agent.

6. The antibody or antigen-binding fragment thereof according to claim 5, wherein the cytotoxic agent is selected from the group consisting of a radiotherapeutic agent, a ribosome-inactivating protein (RIP), a chemotherapeutic agent, a cytotoxic small molecule, a cytotoxic peptide, and a cytotoxic protein.

7. The antibody or antigen-binding fragment according to claim 1, wherein said polypeptide comprises the amino acid sequence of SEQ ID NO: 4506.

8. The antibody or antigen-binding fragment according to claim 7, wherein the antibody is a polyclonal antibody.

9. The antibody or antigen-binding fragment according to claim 7, wherein the antibody is a monoclonal antibody.

10. The antibody or antigen-binding fragment according to claim 9, wherein the antibody or antibody fragment is conjugated to a cytotoxic agent.

* * * * *